United States Patent
Steadman Booker et al.

(10) Patent No.: US 10,539,688 B2
(45) Date of Patent: Jan. 21, 2020

(54) X-RAY DETECTION OF X-RAY INCIDENT FRINGE PATTERN IN PHASE-CONTRAST AND/OR DARK-FIELD X-RAY IMAGING

(71) Applicant: KONINKLIJKE PHILIPS N.V., Eindhoven (NL)

(72) Inventors: Roger Steadman Booker, Aachen (DE); Ewald Roessl, Ellerau (DE); Walter Ruetten, Linnich (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/335,819

(22) PCT Filed: Aug. 3, 2018

(86) PCT No.: PCT/EP2018/071847
§ 371 (c)(1),
(2) Date: Mar. 22, 2019

(87) PCT Pub. No.: WO2019/038113
PCT Pub. Date: Feb. 28, 2019

(65) Prior Publication Data
US 2019/0219713 A1    Jul. 18, 2019

(30) Foreign Application Priority Data
Aug. 23, 2017 (EP) .................... 17187475

(51) Int. Cl.
*G01T 1/20* (2006.01)
*G01T 1/208* (2006.01)
*G01T 1/24* (2006.01)

(52) U.S. Cl.
CPC .......... *G01T 1/2018* (2013.01); *G01T 1/2008* (2013.01); *G01T 1/208* (2013.01); *G01T 1/24* (2013.01)

(58) Field of Classification Search
CPC ..... G01T 1/2008; G01T 1/2018; G01T 1/208; G01T 1/24
See application file for complete search history.

(56) References Cited

U.S. PATENT DOCUMENTS 7,486,770 B2 * 2/2009 Baumann ............... A61B 6/032
378/145
7,492,871 B2    2/2009 Popescu
(Continued)

FOREIGN PATENT DOCUMENTS

| DE | 102012217286 A1 | 3/2014 |
|---|---|---|
| WO | WO2011096584 A1 | 8/2011 |
| WO | WO2017013153 A1 | 1/2017 |

OTHER PUBLICATIONS

Steadman R. et al., "A High Dynamic Range Current-Mode Amplifier for Computed Tomography." Solid-State Circuits, IEEE Journal of Solid-State Circuits, vol. 41, issue 7, pp. 1615-1619, Jul. 2006.
(Continued)

*Primary Examiner* — Marcus H Taningco
(74) *Attorney, Agent, or Firm* — Larry Liberchuk

(57) ABSTRACT

In a conventional phase-contrast X-ray imaging system, a source grating G0 generates an array of partially coherent line sources which illuminate an object and thereafter phase grating G1. The periodicity in the phase grating is self-imaged at certain instances further away from the X-ray source and sampled by a mechanically movable third absorptive analyzer grating G2 before the demodulated fringe intensity is detected by a conventional X-5 ray detector. This application proposes to directly demodulate the fringe intensity using a structured scintillator having a plurality of slabs in alignment with sub-pixels of an optical detector layer, in combination with electronic signal readout approaches. Therefore, a mechanically movable third
(Continued)

absorptive analyzer grating G2 can be omitted from a phase-contrast X-ray imaging system.

14 Claims, 10 Drawing Sheets

(56) References Cited

U.S. PATENT DOCUMENTS

| | | | | |
|---|---|---|---|---|
| 7,639,786 | B2* | 12/2009 | Baumann | A61B 6/484 |
| | | | | 378/145 |
| 8,431,902 | B2* | 4/2013 | Nakatsugawa | A61B 6/4208 |
| | | | | 250/361 R |
| 2007/0183580 | A1* | 8/2007 | Popescu | A61B 6/00 |
| | | | | 378/145 |
| 2012/0183124 | A1 | 7/2012 | Kaneko | |
| 2013/0235973 | A1* | 9/2013 | Murakoshi | A61B 6/4233 |
| | | | | 378/37 |
| 2014/0177795 | A1* | 6/2014 | Spahn | A61B 6/484 |
| | | | | 378/62 |
| 2014/0341347 | A1* | 11/2014 | Radicke | G01N 23/04 |
| | | | | 378/62 |

OTHER PUBLICATIONS

Donath T. et al., "Inverse geometry for grating-based X-ray phase-contrast imaging" by Donath et. al, in the Journal of Applied Physics, 106, 054703 (2009).

* cited by examiner

X-RAY DETECTION OF X-RAY INCIDENT FRINGE PATTERN IN PHASE-CONTRAST AND/OR DARK-FIELD X-RAY IMAGING

FIELD OF THE INVENTION

The present invention relates to X-ray detection. In particular, an X-ray detector for sampling an incident X-ray fringe pattern in phase-contrast and/or dark-field X-ray imaging is discussed, as well as an associated method, interferometer, X-ray imaging system, computer program element, and computer readable medium.

BACKGROUND OF THE INVENTION

Phase contrast imaging has gained considerable attention in medical imaging in the past decade in view of the recently discovered applicability to that field of sophisticated X-ray optics, without the need for changing conventional source or detector hardware. Phase contrast imaging applies Talbot-Lau interferometry, and usually features three diffractive or absorptive X-ray optical elements. Interference fringes formed at a scale of micro-metres or tens of micro-metres can be probed, and phase and small-angle scatter effects of an object of interest can be probed. This has enabled new and medically useful information to be extracted from X-ray images.

US patent publication US 2014/0177795 A1 discusses the application of a Talbot-Lau interferometer to an X-ray imaging system. Such an approach can, however, be further improved.

SUMMARY OF THE INVENTION

There is, therefore, a need to improve X-ray detectors applicable to phase contrast and X-ray imaging. The object of the present invention is solved by the subject-matter of the appended independent claims, wherein further embodiments are incorporated in the dependent claims.

According to a first aspect, there is provided an X-ray detector for sampling an incident X-ray fringe pattern in phase contrast and/or dark-field X-ray imaging. The X-ray detector comprises:

a structured scintillator layer comprising a plurality of slabs arranged to sample the incident fringe pattern and convert it into a plurality of optical slab signals;

an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer; and a signal combination arrangement arranged to electronically read-out signals representing the fringe pattern from the plurality of sub-pixels.

The sub-pixels further comprise a plurality of optical detection cells configured to provide a plurality of detection signals based on the presence of related optical slab signals.

The signal combination arrangement is configured to enable the acquisition of phase contrast and/or dark field X-ray images at a first and second detection direction without adjusting the position of the X-ray detector by generating at least first and second output signals as combinations of the detection signals of the optical detection cells of the optical detector layer. The at least first and second output signals are each proportional to a spatial signal amplitude due to the incident X-ray fringe pattern received on a respective slab of the structured scintillator layer, and a pixel signal of the X-ray detector comprises at least first and second output signals acquired from at least two adjacent sub-pixels at a fringe sampling resolution defined by a width of the slabs.

An effect of this X-ray detector is that the analyzer grating typically denoted $G_2$ and placed in front of a conventional X-ray detector can be omitted from the X-ray interferometer setup, thus allowing the direct detection of fringe phase and fringe visibility information. The implied increased resolution of the direct fringe measurement approach leads to a significant shrinkage of the sub-pixels of the X-ray detector. The limit on detector noise is a physical limit which does not reduce as the size of the sub-pixels reduces. Therefore, the shrinkage of sub-pixels leads proportionally to increased detector noise, which the present approach can improve. The increase in X-ray detector resolution also implies a commensurate increase in X-ray detector information output. The read-out concepts detailed herein can improve the handling of the output signals.

Optionally, the optical detection cell comprises one, or a plurality of silicon photomultipliers configured to detect the respective optical slab signal emitted from the respective slab of the structured scintillator layer.

Silicon photomultiplier (SiPM) cells have fast transient times, typically lower than 1 ns, and quenching times on the order of a few tens of nanoseconds. As such, the use of silicon photomultipliers in phase-contrast X-ray detectors advantageously means that the energy of an incident photon does not need to be resolved, but only the signal amplitude at fine pitch intervals. Therefore, a small number of silicon photomultiplier cells (in the limit, single silicon photomultiplier cell) is functionally adequate to enable phase contrast imaging.

Optionally, the signal combination arrangement is configurable into a first mode in which the first and second output signals are acquired from a first set of adjacent sub-pixels, and configurable into a second mode in which the first and second output signals are acquired from a second set of adjacent sub-pixels, wherein the first and second sets of sub-pixels are aligned at an angle with respect to each other, thus enabling sub-pixel accumulation in different directions without adjusting the position of the X-ray detector.

Optionally, the angle that the first and second sets of sub-pixels are aligned at is 90° (in other words, the sub-pixels of the first and second sets of sub-pixels form a rectangular grid). Optionally, the first and second sets of sub-pixels are aligned at an interior angle of between 0° and 90° to each other. Optionally, the first and second sets of sub-pixels are aligned at an interior angle of between 0° and 80° to each other. Optionally, the first and second sets of sub-pixels are aligned at an interior angle of between 0° and 60° to each other. Optionally, the first and second sets of sub-pixels are aligned at an interior angle of between 0° and 30°. Accordingly, fringe patterns may be sampled in many different directions.

In this way, a direct fringe detector may be provided with the capability of selectively arranging the sub-pixel binning such that the preferred direction to resolve fine structures is defined prior to acquisition. This permits the acquisition of phase contrast images or dark-field images, for example, at a first and a second direction (for example, in perpendicular directions) without needing to move the patient and/or the detector hardware. As such, more accurate X-ray images may be generated, because resolution and patient-detector alignment are not lost by moving the patient or the detector array.

Optionally, the plurality of optical detection cells in one sub-pixel is electrically connected in parallel to generate, in operation, a signal proportional to the number of optical detection cells triggered by an optical emission from a slab of the structured scintillator layer.

Each slab may have a large number of underlying optical detection elements. An effect of the present embodiment is that the large amount of information from the sub-pixels required to be processed can be reduced.

Optionally, the structured scintillator further comprises a first scintillator element and a second scintillator element each formed from different scintillator materials having a different decay time constant to each other. The signal combination arrangement further comprises a first and a second event validation filter matched to the decay time constants of the first and second scintillator elements, to discriminate whether or not the first and second optical detector signals result from optical crosstalk.

The acquired X-ray fringe pattern may be indistinct in time or space (smeared) when signal from first scintillator slab induces optical detector elements underlying neighboring scintillator slabs to activate. The use of different scintillator materials arranged in alternate slabs, wherein the different scintillator materials have different decay time constants, enables signals originating from the first scintillator slab to have a significantly different time-scale footprint than a second scintillator signal originating from the immediately adjacent scintillator slab. Therefore, the signals from adjacent scintillator slabs may be discriminated from each other by monitoring the decay time constant of the received signals. This enables better separation of signals caused by crosstalk from fringe signals.

Optionally, the signal combination arrangement further comprises a complementary event validation filter associated with each sub-pixel, configured to provide a signal related to an optical emission from a neighboring sub-pixel to the neighboring sub-pixel. An effect of this embodiment is improved signal-to-noise ratio, because signals determined to have originated from a neighboring slab are sent to both neighbors, which may use coincidence logic to validate the signal, and add them to their own respective signals.

Optionally, the signal combination arrangement is provided as an analogue circuit. Alternatively, the first and second output signals are digitized, and the signal combination arrangement is provided as a digital signal processing function. Alternatively, the signal combination arrangement is a composite of an analogue circuit and a digital signal processing function.

Optionally, the X-ray detector further comprises a structured color filter layer disposed in-between the structured scintillator layer and the optical detector layer.

The first scintillator element is configured to emit visible light having a first wavelength, and the second scintillator element is configured to emit visible light having a second wavelength, and the structured color filter layer is configured to filter the first and second visible light having respective wavelengths prior to detection in the optical detector layer, to improve crosstalk performance of the optical detector layer.

An effect of this is that corresponding optical detector elements are located underneath different types of scintillator having different scintillation wavelengths. Thus, signal light of a first wavelength originating from the immediately above slab would not be filtered significantly by an optical filter configured to filter light of a second wavelength. However, noise light of the second wavelength originating from an adjacent slab would be filtered significantly by an optical filter configured to filter light of the second wavelength. In this way, the effect of optical crosstalk between slabs is further reduced.

Optionally, the X-ray detector further comprises a scintillator isolation arrangement formed in the structured scintillator layer as an optically-isolating matrix surrounding each slab to improve crosstalk performance of the optical detector layer.

An effect is that optical crosstalk between slabs having scintillator materials of different types is reduced, because the leakage of noise light from adjacent scintillator slabs is reduced.

Optionally, the slab width is in one of the ranges 0.5 to 50 µm, 0.5 to 40 µm, 0.5 to 30 µm, 0.5 to 20 µm, 5 to 20 µm, 10 to 30 µm, 20 to 50 µm.

Optionally, the structured scintillator layer comprises third or fourth scintillator elements, and the optical detector layer comprises third or fourth sub-pixels each in optical alignment with the third or fourth scintillator elements to improve a fringe sampling resolution.

Although a phase-contrast fringe pattern may be adequately resolved with two independent over-sampled channels, the sampling resolution can be improved, and/or the speed of acquisition can be enhanced, when the spatial oversampling rate of the fringe pattern is increased.

According to an example, there is provided an X-ray detector for sampling an incident X-ray fringe pattern in phase contrast and/or dark-field X-ray imaging. The X-ray detector comprises:

a structured scintillator layer comprising a plurality of slabs arranged to sample the incident fringe pattern and convert it into a plurality of optical slab signals;

an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer; and a signal combination arrangement arranged to electronically read-out signals representing the fringe pattern from the plurality of sub-pixels.

The sub-pixels further comprise a plurality of optical detection cells configured to provide a plurality of detection signals based on the presence of related optical slab signals.

The signal combination arrangement is configured to generate at least first and second output signals as combinations of the detection signals of the optical detection cells of the optical detector layer. The at least first and second output signals are each proportional to a spatial signal amplitude due to the incident X-ray fringe pattern received on a respective slab of the structured scintillator layer, and a pixel signal of the X-ray detector comprises at least first and second output signals acquired from at least two adjacent sub-pixels at a fringe sampling resolution defined by a width of the slabs.

According to a second aspect, there is provided an interferometer for phase contrast or dark-field X-ray imaging. The interferometer comprises:

a phase grating structure; and an X-ray detector according to the first aspect or its optional embodiments.

The phase grating structure and the X-ray detector are arranged in an optical path such that the phase grating structure and the scintillator layer of the X-ray detector form an interferometer arrangement for correlating X-ray radiation.

According to a third aspect, there is provided an X-ray imaging system. The X-ray imaging system comprises
an X-ray source;
an interferometer according to the second aspect; and
a controller.

The controller is configured to activate the X-ray source to thus apply X-ray radiation to an object of interest positionable in the optical path.

The X-ray detector of the interferometer is configured to sample and detect a sampled X-ray wave front.

The controller is configured to electronically read-out signals representing the fringe pattern from the plurality of sub-pixels of the X-ray detector of the interferometer.

Optionally, the X-ray imaging system is an inverse X-ray phase-contrast imaging system in which the distance between a source grating $G_0$ and a phase grating $G_1$ is less than a distance between the phase grating $G_1$ and the X-ray detector.

Optionally, the X-ray imaging system is an X-ray phase-contrast imaging system in which the distance between a source grating $G_0$ and a phase grating $G_1$ is greater than a distance between the phase grating $G_1$ and the X-ray detector.

According to a fourth aspect, there is provided a method for phase contrast X-ray imaging and/or dark-field X-ray imaging, comprising the following steps:

a) generating X-ray radiation to examine an object of interest, and directing the X-ray radiation towards an object of interest;

b) receiving the X-ray radiation which has been phase-modulated by an object of interest at an X-ray detector;

c) converting the modulated X-ray radiation into a plurality of optical slab signals using a structured scintillator layer comprising a plurality of slabs arranged to sample the incident fringe pattern;

d) detecting the plurality of optical slab signals using an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer, wherein the sub-pixels further comprise a plurality of optical detection cells configured to provide a plurality of detection signals based on the presence of related optical slab signals;

e) electronically reading out signals representing the fringe pattern from the plurality of sub-pixels using a signal combination arrangement, wherein the signal combination arrangement is configured to enable the acquisition of phase contrast and/or dark field X-ray images at a first and second detection direction without adjusting the position of the X-ray detector by generating at least first and second output signals as combinations of the detection signals of the optical detection cells of the optical detector layer, wherein the at least first and second output signals are each proportional to a spatial signal amplitude due to the incident X-ray fringe pattern received on a respective slab of the structured scintillator layer, and wherein a pixel signal of the X-ray detector comprises at least first and second output signals acquired from at least two adjacent sub-pixels at a fringe sampling resolution defined by a width of the slabs.

According to a fifth aspect computer program element for controlling the X-ray imaging system according to the third aspect which, when being executed by a processing unit, is adapted to perform the method steps of the fourth aspect.

According to a sixth aspect, there is provided a computer readable medium having stored the computer program element of the fifth aspect.

In this description, the term "X-ray phase-contrast imaging" refers to an X-ray imaging technique in which an X-ray source is directed at an object of interest, and a phase grating is used to generate a fringe pattern at regular distances away from the phase grating. A conventional X-ray phase-contrast imaging system typically includes a source grating G0 directly in front of the source, a phase grating G1 located in the X-ray beam generator fringe pattern, and an analyzer grating G2 provided to sample the fringe pattern directly in front of an X-ray detector.

In a conventional X-ray phase-contrast system, the distance between the phase grating G1 and the analyzer grating G2 is smaller than the distance between the source grating G0 and the phase grating G1. In this approach, the analyzer grating G2 must typically have a very fine pitch compared to the phase grating G1 and the source grating G0.

In an "inverse" X-ray phase-contrast system, the distance between the source grating G0 and the phase grating G1 is smaller than the distance between the phase grating G1 and the analyzer grating G2. This enables G2 to have a larger area and coarser structures, presenting less challenging fabrication issues. These aspects are further discussed in the paper "*Inverse geometry for grating-based X-ray phase-contrast imaging*" by Donath et. al, in the Journal of Applied Physics, 106, 054703 (2009).

The detector technique discussed herein is applicable both to conventional and to inverse X-ray phase-contrast systems, as well as many other variations of the optics of X-ray phase-contrast systems coming within the knowledge of a skilled person. However, a concept of this application is to replace the analyzer grating with a structured scintillator forming part of the X-ray detector, and not an analyzer grating. An "inverse" or "conventional" X-ray phase contrast system in this application should be viewed accordingly.

In this description, the term "X-ray fringe pattern" refers to a concept in X-ray grating-based imaging. The standard method involves illuminating a sample with a coherent plane wave front of X-rays. The other side of the sample is provided with a phase grating which establishes a periodic wave front after a propagation distance referred to as the Talbot length. In one approach, the periodic wave front is sampled by moving an analyzer grating across the Talbot pattern in an analyzer direction (known as "phase stepping"). The term X-ray fringe pattern refers to the Talbot pattern.

In this description, term "structured scintillator layer" means a planar or substantially planar layer comprising an array of periodically arranged scintillator channels. Each independent scintillator channel of the structured scintillator is referred to as a "slab". The slabs are arranged with a width, or pitch, to form an analogue of an analyzer grating structure. In other words, the structured scintillator can be considered to replace the function of a traditional analyzer grating structure. Alternatively, the scintillator layer is referred to as a micro-structured scintillator layer. Optionally, the slabs are micro-columns in a structured scintillator material. The micro-columns are parallel, needle-like structures, which optionally have a diameter from 250 nm to 10 µm. The structured scintillator material may be prepared, for example, by vacuum evaporation. Alternatively, the scintillator material is etched into silicon to manufacture a matrix filled with a scintillator material, such as thallium doped caesium iodide, Gadolinium oxysulfide ($Gd_2O_2S$—known as GOS), Gadolinium oxyorthosilicate ($Gd_2SiO_5$—known as GSO), Lutetium-yttrium oxyorthosilicate ($Lu_{2(1-x)}Y_{2x}SiO_5$)—known as LYSO, $Gd_3Al_2Ga_3O_{12}$, known as GAGG, or $Bi_4Ge_3O_{12}$, known as BGO. Many other scintillator materials occurring to the skilled person could be used.

In this description, the term "optical slab signals" refers to bursts of visible light emitted from the structured scintillator layer or its slabs when X-ray photons impinge on a scintillator slab.

In the following description, the term "pixel" refers to an optical light detecting unit having a conventional pixel size, for example of 200 μm×200 μm, although a pixel size having a dimension of up to 1 mm square could be considered. A pixel is structured into sub-pixels such that the fringe pattern may be over sampled by the structured scintillator. During operation, adjacent sub-pixels receive signals having mutually shifted phases.

In the following description, the term "optical detector layer" refers to a semiconductor structure capable of converting optical slab signals from the structured scintillator into electrical signals for processing by the signal combination arrangement. For example, the optical detector layer would typically be formed as a CMOS layer comprising detection components and bus connections, with the structured scintillator layer deposited on top of the CMOS layer. Before deposition of the structured scintillator layer, optical detector elements such as a plurality of silicon photomultipliers, or a plurality of photodiodes, with associated signal combination circuitry, are provided in the CMOS layer.

In the following description, the term "signal combination arrangement" refers to analogue or digital circuitry which functions to read out detection signals. An analogue circuit might, for example, include simple connections in parallel of photomultipliers or photodiodes along horizontal or vertical detection directions in the optical detector layer. Alternatively, or in addition, such analogue circuitry could extend to analogue elements such as a current mirror, a current amplifier, or a current summing amplifier. Alternatively, the signal combination arrangement uses an analogue to digital converter to digitize detection signals close to the optical detector layer. Combination of adjacent signals, for example, can then take place using digital processing, which may be more accurate, and less prone to noise interference.

Thus, it is a basic idea to spatially sample, and/or over sample an X-ray fringe pattern by providing a structured scintillator capable of spatially sampling and/or oversampling the X-ray fringe pattern, in combination with sub-pixels which are aligned with the slabs of the structured scintillator. This enables separation of the fringe pattern from adjacent scintillator slabs.

These and other aspects of the present invention will become apparent from and elucidated with reference to the embodiments described hereinafter.

BRIEF DESCRIPTION OF THE DRAWINGS

Exemplary embodiments of the invention will be described in the following drawings. Electrical circuit schematics in the drawings are presented for their topological information rather than to present a finished electronic design. The skilled person would, however, be able to complete a finished design with reference to the schematics.

DETAILED DESCRIPTION OF EMBODIMENTS

The traditional X-ray approach uses an X-ray source to illuminate the front of an object of interest. An X-ray detector, such as a digital detector is positioned at the rear of the object of interest. Materials in the object of interest having different densities will cause non-uniform absorption of the X-ray wave front. The digital detector provides an absorption image of the internal structure of the object of interest based on the varying absorption of the X-ray wave front.

Significant attention is now being directed towards phase contrast X-ray imaging. Materials in the object of interest affect the absorption of an X-ray wave front, but typically they also affect the phase shift of an X-ray wave front. Particularly in the case of soft tissue imaging, detection of a phase difference can provide image of better quality than that obtained by traditional absorption imaging. Alternatively, the patient dose can be reduced.

Figure 1:
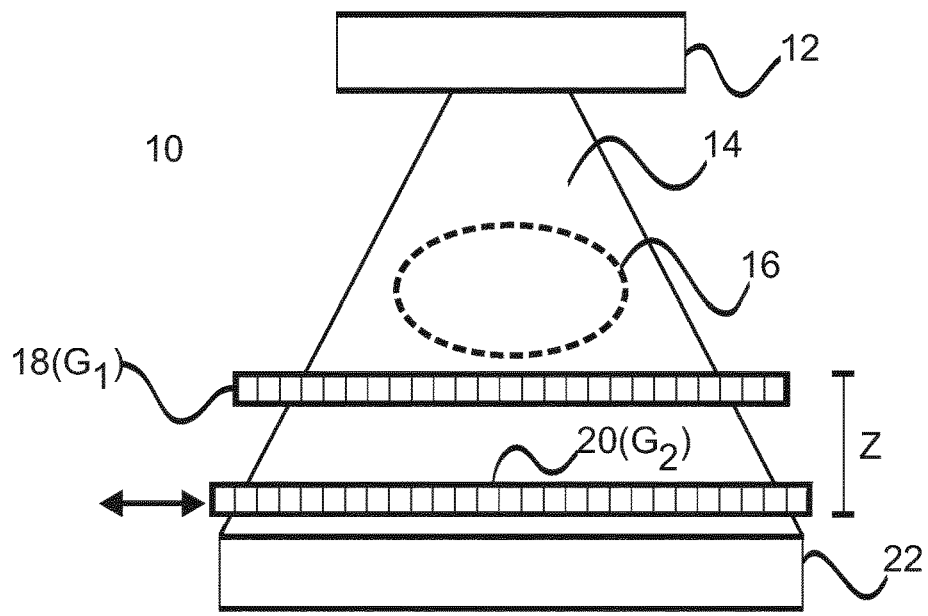
FIG. 1 illustrates a schematic side view of a conventional phase-contrast imaging system.

FIG. 1 illustrates a conventional X-ray phase contrast imaging approach. In particular, a basic grating-based X-ray interferometer 10 is shown. An alternative name for the illustrated arrangement is an X-ray Talbot interferometer. This comprises a highly coherent X-ray source 12 which emits an X-ray beam 14 in the direction of an object of interest 16. At the rear of the object of interest, phase grating 18 ($G_1$) and an analyzer grating 20 ($G_2$) are provided in alignment with each other. The analyzer grating 20 ($G_2$) is movable using a mechanism (not shown). A digital X-ray detector 22 is positioned to receive and sample the amplitude or variations of the X-ray fringe pattern having travelled through the object of interest 16, phase grating 18, and the analyzer grating 20.

Optionally, the highly coherent X-ray source 12 is provided as a conventional polychromatic X-ray source (such as a rotating anode X-ray tube) in combination with a source grating $G_0$, forming a Talbot-Lau interferometer when placed in the wider system.

An X-ray Talbot interferometer exploits the X-ray Talbot effect, which is also known as a self-imaging effect. Phase grating 18 is a periodic structure, and when placed under highly coherent illumination by the X-ray source 12, creates self-images of the phase grating 18 at specific distances away from the phase grating 18. This phenomenon is consequence of Fresnel diffraction. Under partially coherent X-ray illumination, the visibility of the self-image may be degraded, but may still be useful.

An incident X-ray wave is deformed due to the phase shift caused by an object of interest 16 positioned in front of the phase grating 18. This also causes the self-image to be deformed according to phase inhomogeneities in the object of interest 16. The amount of deformation in the self-image is proportional to the distance, z, away from the phase grating 18 at which the self-image is sampled. Conventionally, the digital X-ray detector 22 does not have sufficient resolution to directly sample the self-image. Therefore, in conventional arrangements, an analyzer grating 20 is also provided. If the period of the analyzer grating 20 is comparable to that of the self-image, a superposition of the self-image (deformed by the object of interest 16) and the pattern of the analyzer grating 20 results (commonly called a Moirè fringe pattern). The deformation of the self-image caused by phase inhomogeneities in the object of interest 16 results in further deformation of the Moirè fringe pattern.

Conventionally, fringe spacing is large enough to enable normal digital X-ray image detectors to detect portions of the fringe pattern sampled by the analyzer grating 20.

This approach requires the analyzer grating 20 to be physically movable across the fringe pattern for a number of steps, sampling the amplitude of the deformed self-image to enable the complete capture of the phase profile of the object of interest 16. Such a mechanically movable analyzer grating 20 is undesirable because it results in additional machine design complexity, and causes X-ray examinations to last longer. This is a problem when imaging regions in the body which move quickly, for example during heart imaging.

Furthermore, the analyzer grating 20 is an absorbing grating, causing loss of X-ray radiation that has already passed the object of interest. This is undesirable because it leads to a higher radiation dose to a patient.

Figure 2:
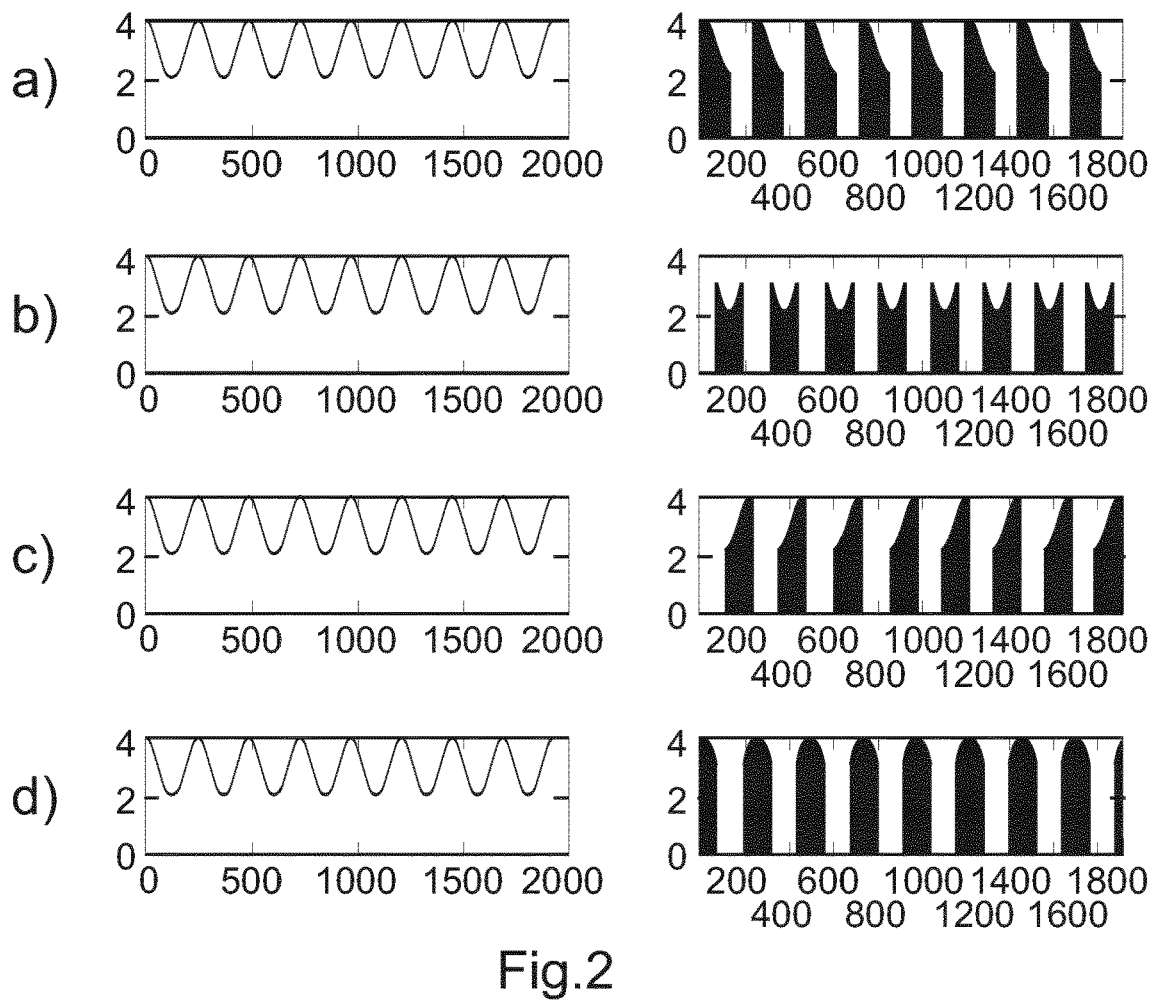
FIG. 2 illustrates exemplary sampled intensity patterns from a four-channel conventional phase-contrast imaging system.

FIG. 2 illustrates an exemplary sampling pattern associated with the conventional phase stepping method illustrated in FIG. 1. In the graphs of FIG. 2, the ordinate represents an arbitrary distance unit across a portion of a digital X-ray detector, and the abscissa represents arbitrary X-ray intensity received at the corresponding portion of a digital X-ray detector. The left-hand side column of graphs shows the incident X-ray intensity prior to an analyzer grating structure 20. The four graphs a) to d) in the right-hand column of FIG. 2 illustrate the X-ray signals in the respective left-hand column having been filtered by the analyzer grating 20 at four different analyzer grating offset distances. In other words, the right-hand column of FIG. 2 illustrates the signals of four different phase groups as they appear at an X-ray detector 22.

Figure 3:
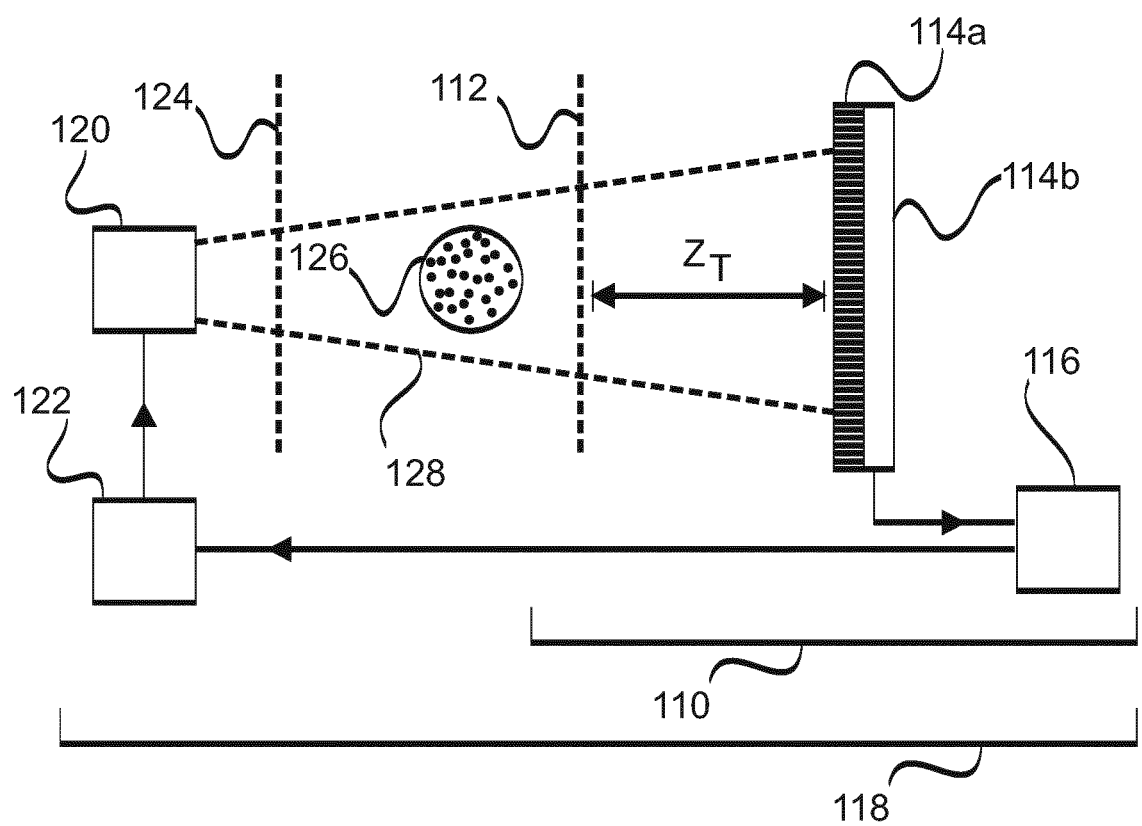
FIG. 3 illustrates schematically a side-view of an X-ray phase-contrast interferometer, and an X-ray phase-contrast imaging system incorporating the interferometer according to the second and third aspects.

To introduce the context of the invention, FIG. 3 illustrates an interferometer 110 according to a second aspect incorporated within an X-ray imaging system 118 according to a third aspect. Of course, the interferometer 110 may be provided as a separate item to the X-ray imaging system 118, and the illustrated combination of the two elements is for convenience, and not limiting. The interferometer 110 and the X-ray imaging system 118 will be more fully explained subsequently.

A phase grating structure 112 $G_1$ is arranged across an X-ray beam which has passed through an object of interest 126. An X-ray detector 114a, 114b is arranged such that its structured scintillator 114a faces phase grating structure 112 $G_1$. For example, the X-ray detector 114A, 114B is optionally separated from the phase grating structure 112 $G_1$ by a Talbot distance $Z_T$, or a fractional Talbot distance. The structured scintillator 114a samples (or over samples) the amplitude of an X-ray fringe pattern generated by the interaction of X-rays with the phase grating structure 112, and the object of interest 126. By sampling the amplitude of the X-ray fringe pattern, the structured scintillator 114a enables detection of phase changes of the X-ray beam 128 caused by the object of interest 126. Signal combination circuit 116 generates first and second output signals from the X-ray detector 114a, 114b.

Figure 4:
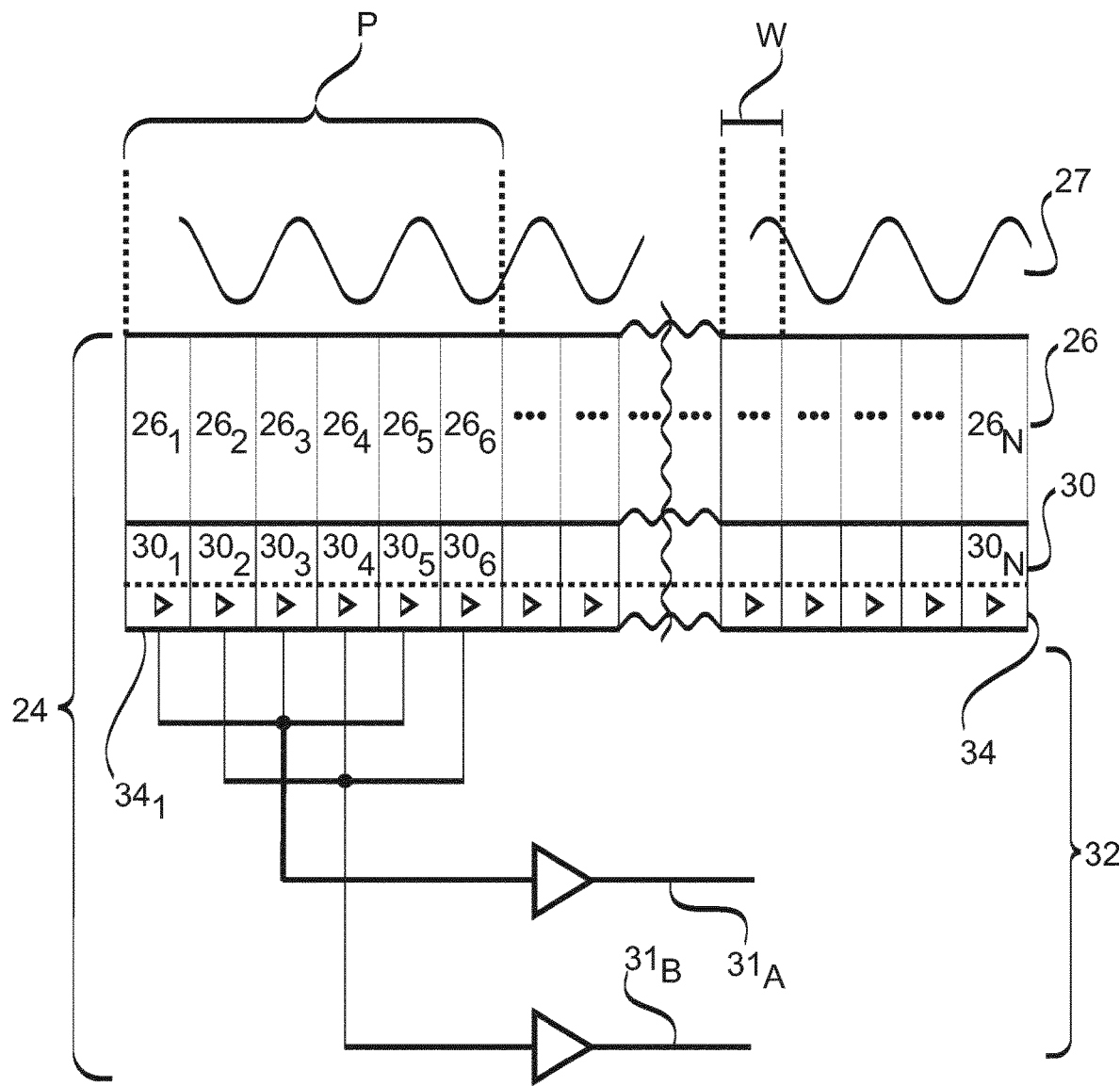
FIG. 4 illustrates a schematic view of an X-ray detector according to a first aspect.

FIG. 4 illustrates an X-ray detector 24 for sampling an incident X-ray fringe pattern 27 in phase contrast and/or dark-field X-ray imaging according to the first aspect. Optionally, the X-ray detector is intended to be comprised within an interferometer 110 according to a second aspect incorporated within an X-ray imaging system 118 according to a third aspect. The X-ray detector 24 comprises a structured scintillator layer 26 comprising a plurality of slabs $26_1$, $26_2$, ..., $26_N$, arranged to sample the incident fringe pattern 27 and to convert it into a plurality of optical slab signals.

The X-ray detector 24 also comprises an optical detector layer 30 in optical communication with a structured scintillator layer 26. The optical detector layer 30 comprises a plurality of sub-pixels $30_1$, $30_2$, ..., $30_N$. Each sub-pixel is aligned with a respective slab $26_1$, $26_2$, ..., $26_N$ of the structured scintillator layer, to detect a respective optical slab signal emitted from a respective slab $26_1$, $26_2$, ..., $26_N$ of the structured scintillator layer.

The X-ray detector 24 also comprises a signal combination arrangement 32 arranged to electronically read out signals representing the fringe pattern 27 from the plurality of sub-pixels 30.

The optical detector layer 30 further comprises a plurality of optical detection cells 34 configured to provide a plurality of detection signals based on the presence of related optical slab signals.

The signal combination arrangement 32 is configured to generate at least first $31_A$ and second $31_B$ output signals as combinations of the detection signals of the optical detection cells 34 of the optical detector layer 30. The at least first $31_A$ and second $31_B$ output signals are each proportional to a spatial signal amplitude due to the incident X-ray fringe pattern 27 received on a respective slab $26_1$, $26_2$, ..., $26_N$ of the structured scintillator layer. A pixel signal of the X-ray detector 24 comprises at least first $31_A$ and second $31_B$ output signals acquired from at least two adjacent sub-pixels at a fringe sampling resolution defined by a width W of the slabs. In the embodiment of FIG. 4, the slab width W is substantially one half of the fringe period of the incident X-ray radiation 27.

Thus, it is a basic idea to use a structured scintillator array 26 in combination with an optical detector layer 30 and a signal combination arrangement 32 to separate the incident X-ray fringe pattern 27 from adjacent scintillator slabs, to acquire a direct measurement of phase contrast imaging fringe patterns. Individual scintillator slabs $26_1$, $26_2$, ..., $26_N$ are in optical alignment with individual sub-pixels. This removes the need for a mechanically movable analyzer grating. In the illustrated case in FIG. 4, the effect of a mechanically stepped phase grating having to step positions is replaced by monitoring the ratio of the first and second output signals $31_A$, $31_B$.

In FIG. 4, an embodiment of a proposed sensor is shown in which a large pixel P is segmented along one planar direction into six scintillator slabs. The six scintillator slabs are optically coupled to the optical detector layer 30. FIG. 4 also illustrates neighboring pixels.

Optionally, the optical coupling may be achieved using an optical coupling layer in-between the structured scintillator layer 26 and the optical detection layer 30. Optionally, the optical coupling layer is provided as an fibre optic plate (not shown).

Typically, the pixel P, has a width of several hundreds of micro metres, and is segmented into scintillator slabs having a pitch of around 20 to 30 micro metres. The optical detector layer 30 is also made up of a number of pixels having the same dimensions. Each pixel of the optical detector layer 30 is segmented to match the segmentation of the structured scintillator layer 26. FIG. 4 shows that the optical detector layer 30 is segmented into six sub-pixels along the same direction as the structured scintillator layer 26. The sub-pixels in the optical detector layer 30 are in optical alignment with the slabs of the structured scintillator layer 26. In other words, a relatively high level of incident X-ray radiation at structured scintillator slab $26_1$ will cause this slab to emit a relatively large optical signal into sub-pixel $30_1$ of the optical detector layer 30. However, because the scintillator is structured, the relatively large optical signal from structured scintillator slab $26_1$ does not leak into adjacent sub-pixels of the optical detector layer 30.

In FIG. 4, the first and second output signals $31_A$ and $31_B$ read out the "first" and "second" outputs of the optical detection cells. Optionally two channels could, for example, be designed with the scintillator spacing to readout the first signal as a "peak" fringe value, and the second signal as a "trough" value of the fringe pattern. In the illustrated embodiment, events registered within "even" numbered slabs are accumulated into the first readout channel $31_A$. Likewise, events in "odd" numbered slabs are also registered into the second readout channel $31_B$. In the illustrated embodiment, each pixel P thus acquires two measurements corresponding to the signal level registered in "odd" and "even" slabs.

In the illustrated embodiment of FIG. 4, the choice of scintillator pitch W is provided so that one of the channels contains information from the peaks of the fringe pattern 27, whilst the other channel acquires the troughs of the fringe pattern 27. Therefore, the choice of scintillator pitch W is closely related to the wavelength of the incident X-ray beam of the system that the X-ray detector 24 is used with. This is, however, a minimal case and it will be appreciated that the scintillator pitch W can optionally be designed to oversample the fringe pattern 27. The scintillator pitch W is, thus, designed following similar considerations as would be made in a conventional detector when designing the pitch of the movable analyzer grating.

The ratio between the outputs of the first and second output signals $31_A$ and $31_B$ is therefore indicative of the fringe phase and the fringe visibility. However, the scintillator pitch may optionally be configured to be a fraction of W, such as one third or one quarter of the fringe period, in the case that the structured scintillator is designed to oversample the X-ray fringes. Optionally, the structured scintillator may be designed to oversample the interference fringes 27, which enables the direct detection of phase and scatter information.

Many different optical detection components may be comprised within the optical detection cell.

According to an embodiment, the optical detection cell comprises one, or a plurality of silicon photomultipliers configured to detect the respective optical slab signals emitted from respective slabs of the structured scintillator layer.

Silicon photomultipliers (SiPM) are arrays of solid state avalanche photodiodes (APDs) which are sensitive to single photons, and manufactured on a common silicon substrate.

The silicon photomultipliers of the array and their quenching resistors are optionally connected in parallel. The quenching resistor allow the reverse bias voltage to drop low enough to stop the avalanche after a short time. After that, the APD will again recharge to the full bias voltage via the resistor. Each device works in a digital ("Geiger") mode, although all silicon photomultipliers of the array are read in parallel. Therefore, a silicon photomultiplier generates signals with a variable dynamic range dependent on whether one, or thousands, of photons are received.

The discrete mode of operation of the silicon photomultipliers implies that information concerning the energy of the original optical photon is lost. It is optionally proposed to address this lack of proportionality by providing large silicon photomultiplier pixels having a size of several mm squared, with each silicon photomultiplier pixel optionally having in excess of one thousand silicon photomultiplier cells. The number of silicon photomultiplier cells should be sufficiently high to be able to validate that the detected activity originated from an X-ray interaction event, and not "dark count" events from inside the silicon photomultiplier itself.

Figure 5:
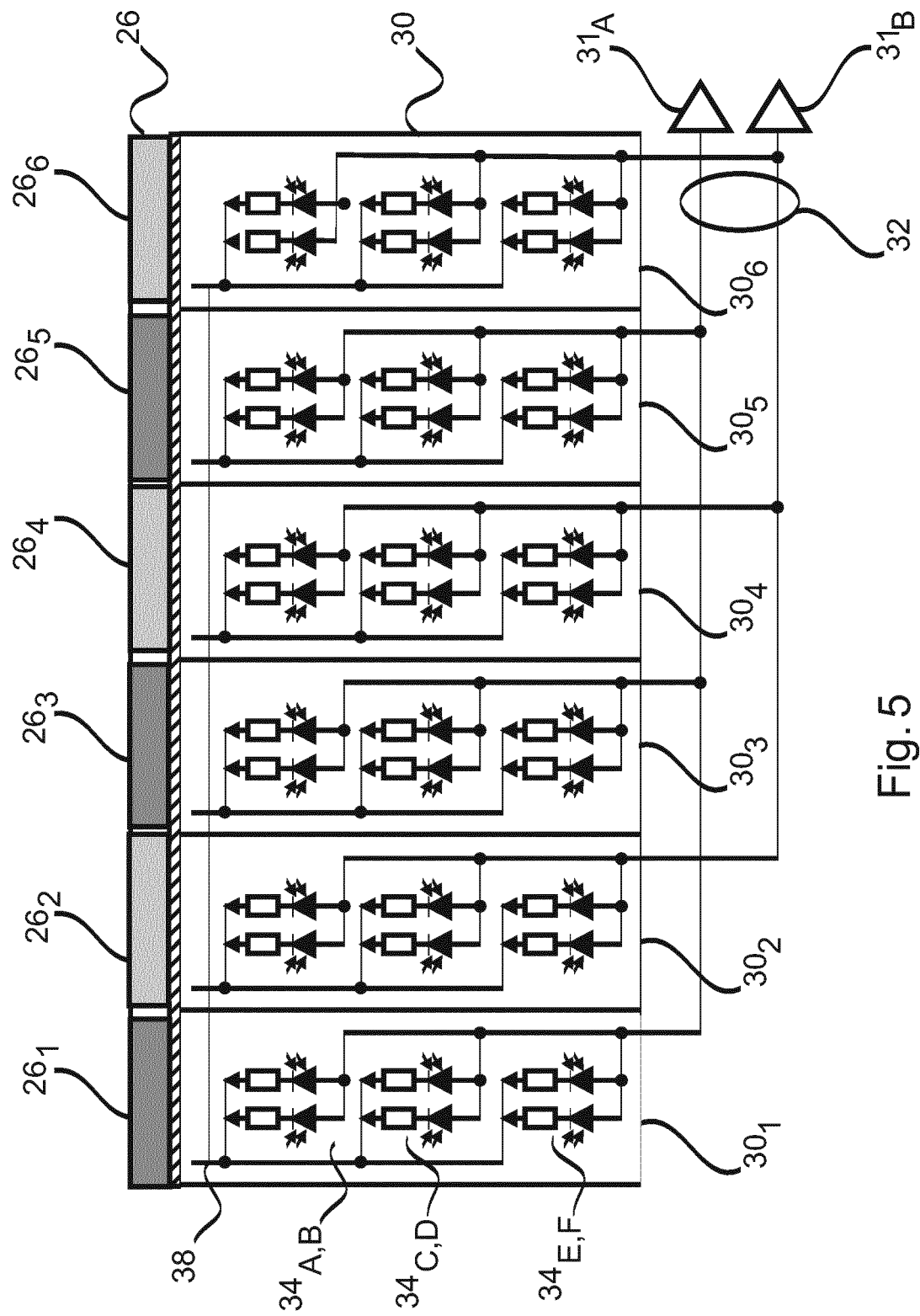
FIG. 5 illustrates a schematic view of a practical embodiment according to a first aspect.

FIG. 5 illustrates a proposed X-ray detector according to an embodiment, using a silicon photomultiplier topology. The alternately shaded slabs represent alternate scintillator slabs located above alternate optical detector layers and signal combination arrangements which are optically coupled to the scintillator slab directly above. FIG. 5 illustrates a single pixel P divided into six structured scintillator slabs $26_1, \ldots, 26_6$ which are in turn optically coupled to six sub-pixels $30_1, \ldots, 30_6$ provided in the optical detector layer 30. Optionally, each silicon photomultiplier has its own quenching resistor. Optionally, an active silicon photomultiplier quenching circuit may be used.

The illustrated topology shows a common-cathode arrangement wherein the diode cathodes of the silicon photomultipliers are connected together to cathode 38. Within each sub-pixel $30_1, \ldots, 30_6$ the anodes of the silicon photomultipliers are connected together. Thus, the current flowing through the anode connection for one sub-pixel corresponds to the sum of current of the silicon photomultipliers that fired in that sub-pixel. The signal combination arrangement 32 in FIG. 5 is the bus connection of the anodes of every second slab into a first signal group $30_1, 30_3, 30_5$ and a second signal group $30_2, 30_4, 30_6$. The practical effect of this is that all of the detected photon events related to the first half of the fringe pitch are summed together to form a first output signal $31_A$, and all of the detected photon events relating to the second half of the fringe pitch are summed together to form a second output signal $31_B$.

Optionally, an X-ray detector 24 is provided, wherein a plurality of optical detection cells 34 associated with one sub-pixel are electrically connected in parallel to generate, in operation, a first and/or second output signal proportional to the number of optical detection cells triggered by an optical emission from a slab of structured scintillator layer 26.

In operation, as a large X-ray flux is experienced at structured scintillator slab $26_1$, a correspondingly large visible light flux is optically transmitted into sub-pixel $30_1$. A large visible light flux will result in a large proportion of the silicon photomultipliers $34_A$, $34_B$, $34_C$, $34_D$, $34_E$, $34_F$ firing, and a correspondingly large current provided as the first output signal $31_A$.

Optionally, the signal combination arrangement may comprise a signal validation circuit (not shown) for each output signal $31_A$, $31_B$. The signal validation circuit is configured to apply a threshold to the first and/or second output signals $31_A$, $31_B$, respectively, to ensure that the silicon photomultipliers report real scintillator interactions, and not dark counts. Thus, a valid event is considered to exist when a certain number of cells have fired within a time interval defined by the scintillator material used. The signal validation circuit may be provided in analogue form as a comparator, or following an analogue to digital conversion stage, as a digital comparator.

Current flowing through the anodes in one sub-pixel underlying a slab corresponds to the sum of current from the silicon photomultipliers in the sub-pixel that fired. Optionally, the anode signal is not shared across multiple sub-pixels underlying a slab, and event validation is performed for each slab enabling the first and second output signals $31_A$, $31_B$ to be a sum of all the validated events.

In the foregoing discussion, a topology involving one pixel having six slabs divided into two alternating slab groups has been discussed. The skilled reader will appreciate that a typical X-ray detector will have many thousands of pixels. The pixels may be subdivided into an arbitrary number of slabs, and that the arbitrary number of slabs may be interconnected to sample the fringes of an incident X-ray with three channels, four channels, five channels, six channels, or more channels. Sampling the fringes of an incident X-ray pattern with higher number of channels enables the fringe pattern to be over sampled, providing enhanced image resolution.

According to an embodiment, an X-ray detector 24 is provided as described previously, wherein the signal combination arrangement is configurable into a first mode in which the first and second output signals $31_A$, $31_B$ are required from the first set of adjacent sub-pixels, and configurable into a second mode in which the first and second output signals are required from a second set of adjacent sub-pixels, wherein the first and second sets of sub-pixels are aligned at an angle with respect to each other, thus enabling sub-pixel accumulation in different directions without adjusting the position of the X-ray detector.

Optionally, the angle that the first and second sets of sub-pixels are aligned at is 90° (in other words, the sub-pixels of the first and second sets of sub-pixels form a rectangular grid). Optionally, the first and second sets of sub-pixels are aligned at an interior angle of between 0° and 90° to each other. Optionally, the first and second sets of sub-pixels are aligned at an interior angle of between 0° and 80° to each other Optionally, the first and second sets of sub-pixels are aligned at an interior angle of between 0° and 60° to each other. Optionally, the first and second sets of sub-pixels are aligned at an interior angle of between 0° and 30°. Accordingly, fringe patterns may be sampled in many different directions.

This application concerns the direct measurement of phase contrast fringes which may eliminate the analyzer grating 20 of the conventional phase contrast imaging system 10. Conventionally, gratings and/or scintillator slabs are arranged such that in order to avoid missing clinically relevant structure in the direction parallel to the gratings or rectangular scintillator slabs, a minimum of two acquisitions is needed, involving rotating the source ($G_0$), phase ($G_1$), and analyzer ($G_2$) gratings by 90°. In the case of using a direct fringe detector with rectangular scintillator slabs, the detector itself would also need to be rotated.

The following embodiment describes an adapted pixel topology for use in phase contrast X-ray detectors which may resolve fine structures without rotating the detector.

Figure 6:
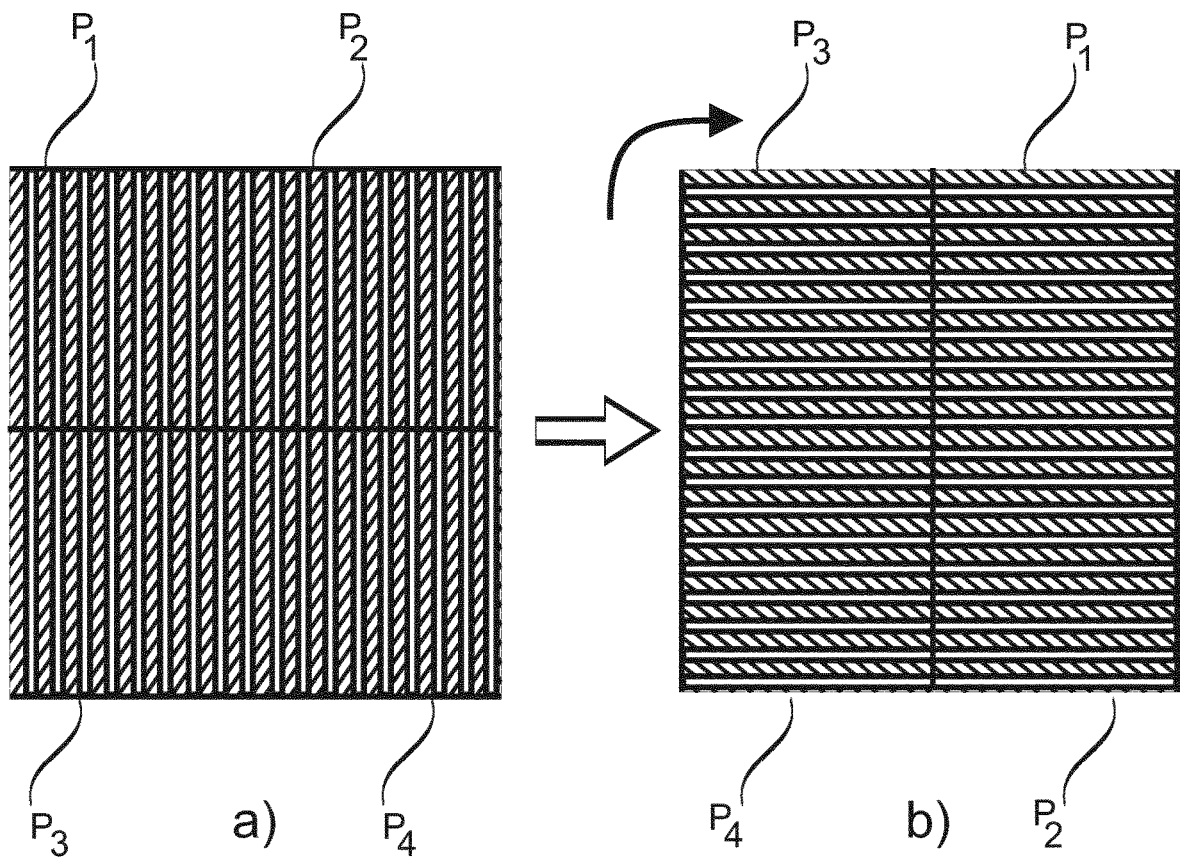
FIG. 6a) illustrates schematically the slabs of a conventional one-dimensional fringe detector.
FIG. 6b) illustrates schematically the slabs of the conventional one-dimensional fringe detector when rotated through ninety degrees FIG. 7a) illustrates the selection of sub-pixels in a 2-D selectable direct fringe detector in a first (vertical) mode according to an embodiment.

FIG. 6a) illustrates a conventional detector topology with four pixels $P_1, \ldots, P_4$. The scintillators overlying the pixels are each structured along one direction. In other words, the two alternating slab channels have a large aspect ratio. Conventionally, this configuration assumes that fine structuring is a long one direction, while a native digital detector pitch may still be used in the other direction. In an example, a conventional pixel size of 200 um by 200 um may be structured into 10 slabs in the x direction, whilst along the y direction, the slab remains structured to its native 200 µm length.

The above topology implies that the detection of fine structures is preferred in one direction. In order to ensure that clinically relevant structures along the other direction are not missed, methods to rotate the gratings (source and phase grating) must be provided. This would require rotating all of the gratings in synchrony, which is difficult to achieve accurately and with an inexpensive mechanical design. It is therefore proposed to introduce a 2-D structured array in combination with an electronic readout circuit capable of selectively arranging sub-pixel binning along other preferred directions.

FIG. 6b) illustrates a conventional slab arrangement which has been turned through ninety degrees.

FIG. 7a) illustrates a finely structured two-dimensional sub-pixelation topology within the boundaries of conventional pixels $P_1, \ldots, P_4$. The sub-pixelation topology comprises a plurality of silicon photomultipliers or photodiodes performing as optical detection cells. The 2-D selectable direct fringe detector is switchable between two modes in which in a first mode the output signal is binned along a first preferred direction, and a second mode in which the signal is binned along a second preferred direction. In FIG. 7a), the 2-D selectable direct fringe detector is shown in a first mode in which a fringe pattern is sampled by four pixels having alternate slab channels in a vertical direction. FIG. 7b) shows a second mode in which a fringe pattern is sampled by four pixels having alternate slab channels in a horizontal direction.

It will be appreciated that an X-ray interferometer and or system configured to use the detector of this embodiment will require a source grating G0 and a phase grating G1 to be rotated by 90° as the changes made between the first mode and the second mode and vice versa.

Figure 7:
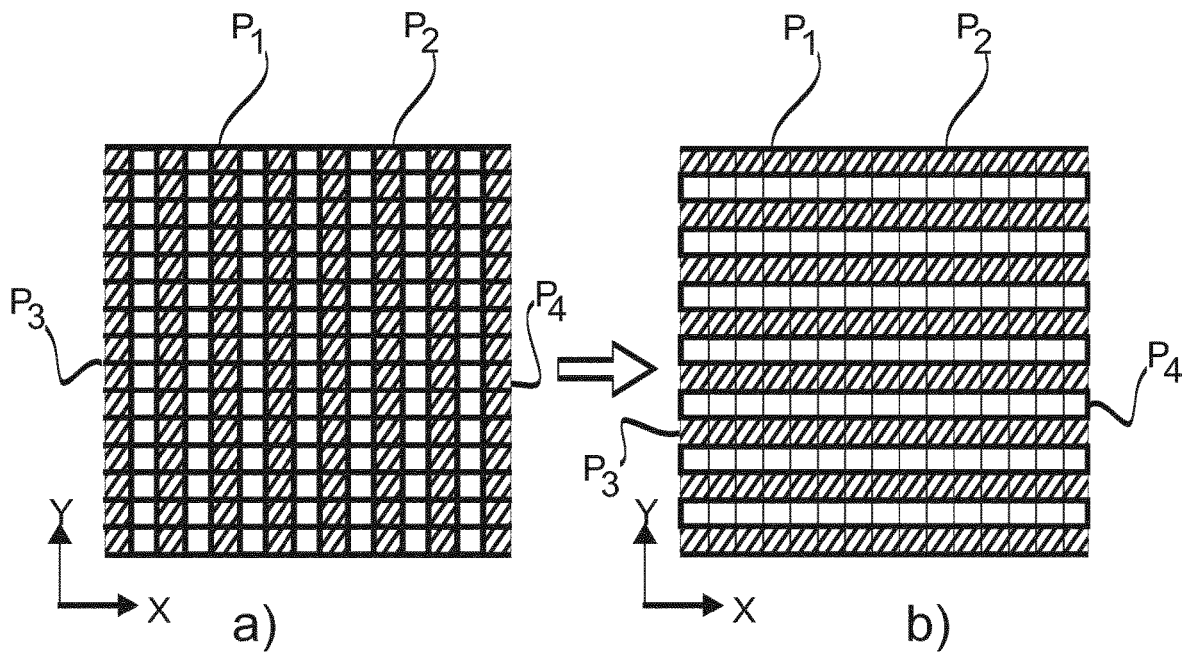
FIG. 7b) illustrates the selection of sub-pixels in a 2-D selectable direct fringe detector in a second (horizontal) mode according to an embodiment.
Figure 8:
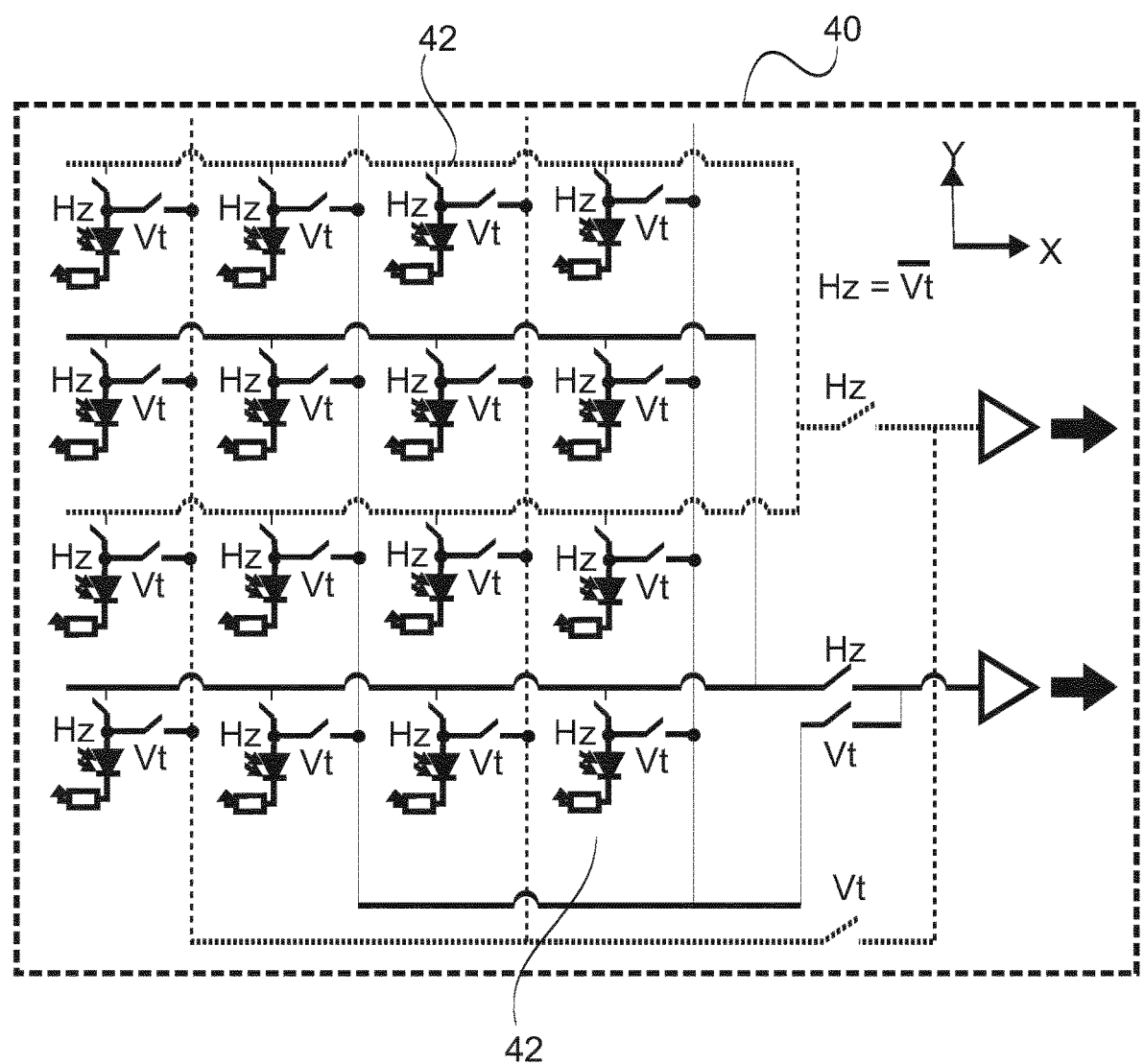
FIG. 8 illustrates an electronic circuit schematic for a 2-D selectable direct fringe detector circuit.

FIG. 8 shows a schematic diagram of a circuit for obtaining selectable vertical and horizontal sub-pixel arrangements for orientation of the fringe sampling as discussed in conceptual terms in relation to FIG. 7 in a non-limiting example where the first and second sets of sub-pixels have a perpendicular alignment to each other in different modes.

The dotted line 40 illustrates a conventional pixel boundary. Within the conventional pixel boundary is a grid of optical detection elements 42 which are optionally (and as illustrated) a plurality of silicon photomultipliers. Optionally, the grid of optical detection elements 42 alternatively, or in combination, comprises photodiodes. In the example of FIG. 8, the cathodes of the silicon photomultipliers are connected to ground, and the anodes of the silicon photomultipliers are connected, via quench resistors, to the Hz and Vt selection switches. The label "Hz" refers to a digital signal indicating horizontal orientation, and the label "Vt" refers to a digital signal indicating vertical orientation. These two signals are complementary.

Optionally, the silicon photomultipliers are provided with active quenching elements.

Optionally, each optical detection element 42 is provided as a parallel network of silicon photomultipliers, as shown in FIG. 5, features 34 A,B. In this case, the output of each parallel network is connected to switches Hz and Vt, respectively.

In FIG. 8, switches relating to Hz and Vt are illustrated as simultaneously in open circuit, but this is solely to provide clarity as to the location of the switches in the schematic. In operation, when the Hz switches are closed-circuit, the Vt switches will be open circuit. When the Hz switches are open-circuit, the Vt switches will be closed-circuit.

In this case, the signal combination arrangement comprises a network of switches Hz and Vt, and buses enabling binning of the first output signal and the second output signal along to preferred directions. When the Hz switches are closed-circuit and the Vt switches are open circuit, alternate horizontal rows of optical detection elements are connected. When the Hz switches are open-circuit and the Vt switches are closed circuit, alternate vertical rows of optical detection elements are connected. Thus, the fringes of an X-ray fringe pattern may be sampled and output as at least a first and second output signals, in horizontal and vertical directions.

This approach may be particularly advantageous when dark-field imaging is performed, for example, because it allows the determination of fine clinical structure in a plurality of directions without complex rearrangement of the patient or X-ray imaging system.

Figure 9:
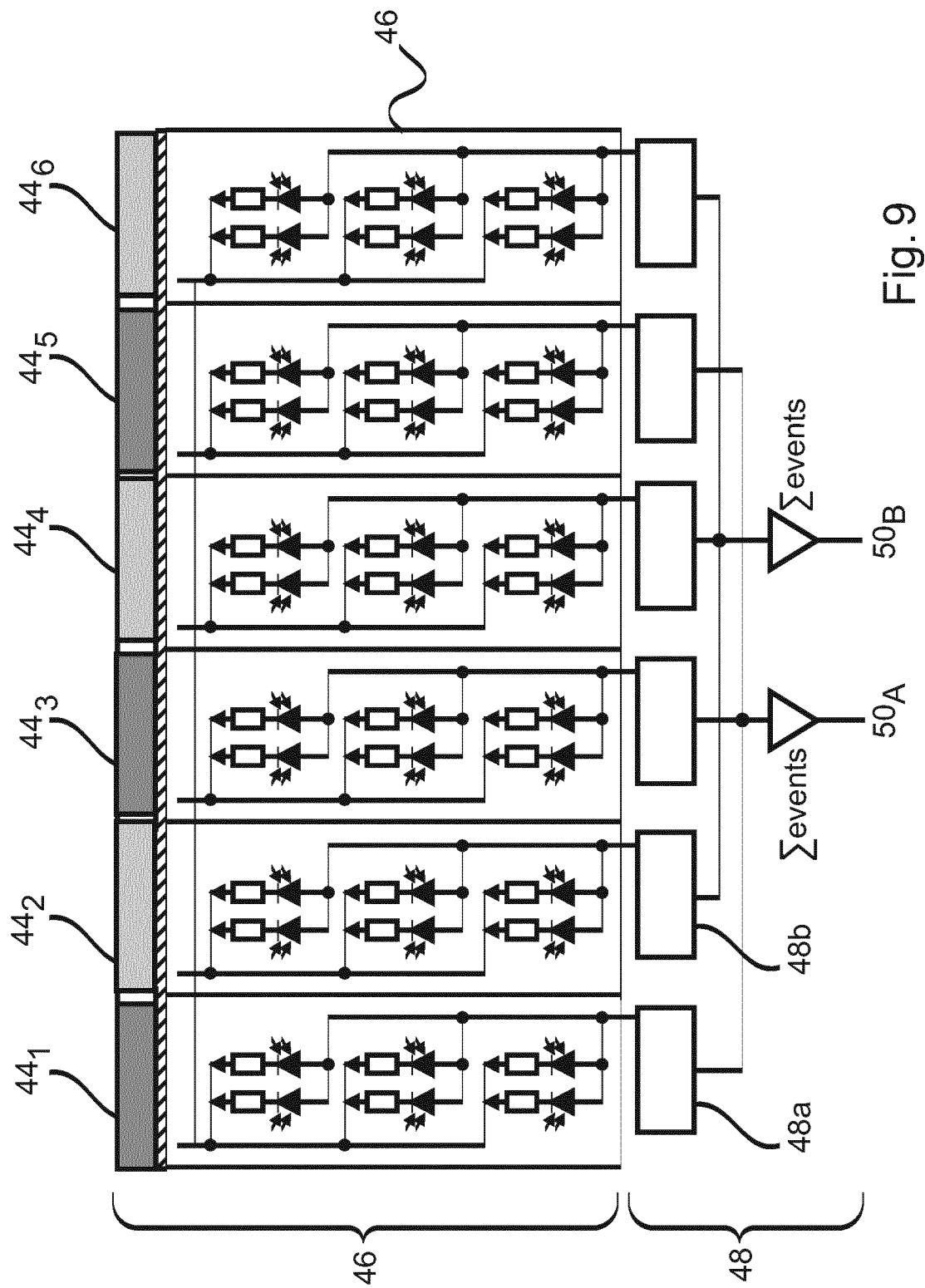
FIG. 9 illustrates schematically further practical embodiment of an X-ray detector having event filtering.

According to an embodiment of the first aspect (a non-limiting example of which is illustrated in FIG. 9), an X-ray detector 24 is provided, wherein the structured scintillator $44_1$, $44_2$, $44_3$, $44_4$, $44_5$, $44_6$ further comprises a first scintillator element $44_1$ and a second scintillator element $44_2$ each formed from different scintillator materials having a different decay time constant to each other. The signal combination arrangement 48 further comprises a first 48a and a second 48b event validation filter.

It is advantageous to reduce optical crosstalk in first and second scintillator slabs, because such crosstalk can smear the acquired fringe pattern. According to this embodiment, it is proposed to use two different types of material in respective alternate scintillator slabs in the structured scintillator.

An example of two different types of scintillator materials having different decay time constants would optionally be BGO and LYSO, as discussed previously, although many other combinations of scintillator material would occur to the skilled person.

Each of the types of the different scintillator materials exhibits a significantly different decay time constant. In other words, the excitation of the optical detection cells in the optical detector layer 46 underlying a slab 44 will cause an accumulated firing pattern as a function of time. Optionally, each individual optical detection cell is configured to refresh independently of the other optical detection cells of the plurality of detection cells. Therefore, individual optical detection cells may re-fire multiple times for a single photon interaction event.

The amplitude of the first or second output signals will exhibit discrete steps. The signals will be, in full-scale, dependent on the number of optical detection cells per scintillator slab.

In the embodiment illustrated in FIG. 9, matched filters 48a, 48b are provided per slab (or optionally one per slab type within a pixel). The matched filters enable discrimination of the signal detected, by a sub-pixel, to distinguish whether the signal originated as a result of the scintillator slab directly above the sub-pixel, or alternatively whether the signal was caused by optical crosstalk from an adjacent scintillator slab.

Optionally, events which are not validated by the digital filters 48a, 48b to have originated from the correct scintillator slab are discarded. Valid events which are identified by digital filters 48a, and 48b which are determined to have originated from the correct slab are used to contribute to the first 50a and/or second 50b output signal for that particular scintillator slab and sub-pixel.

Optionally, discarded signals from a sub-pixel underlying a first scintillator slab are provided to a filter (not shown) for the alternate signal type. Therefore, an output signal attributable to the first scintillator slab $44_1$ may be presented to the corresponding detector circuit of $44_2$, whereas signals determined to have originated from a slab adjacent to the first scintillator slab are provided to the detection circuitry of these adjacent slabs. The detection circuitry of the adjacent slabs may optionally apply coincidence logic (not shown) to validate whether or not the signal rejected from the first scintillator slab has originated from one of the adjacent slabs. If it is determined that the signal has originated from one of the adjacent slabs, the signal is added to the output of that adjacent slab.

In this way, the signal-to-noise ratio of the X-ray detector 24 may be improved.

Figure 10:
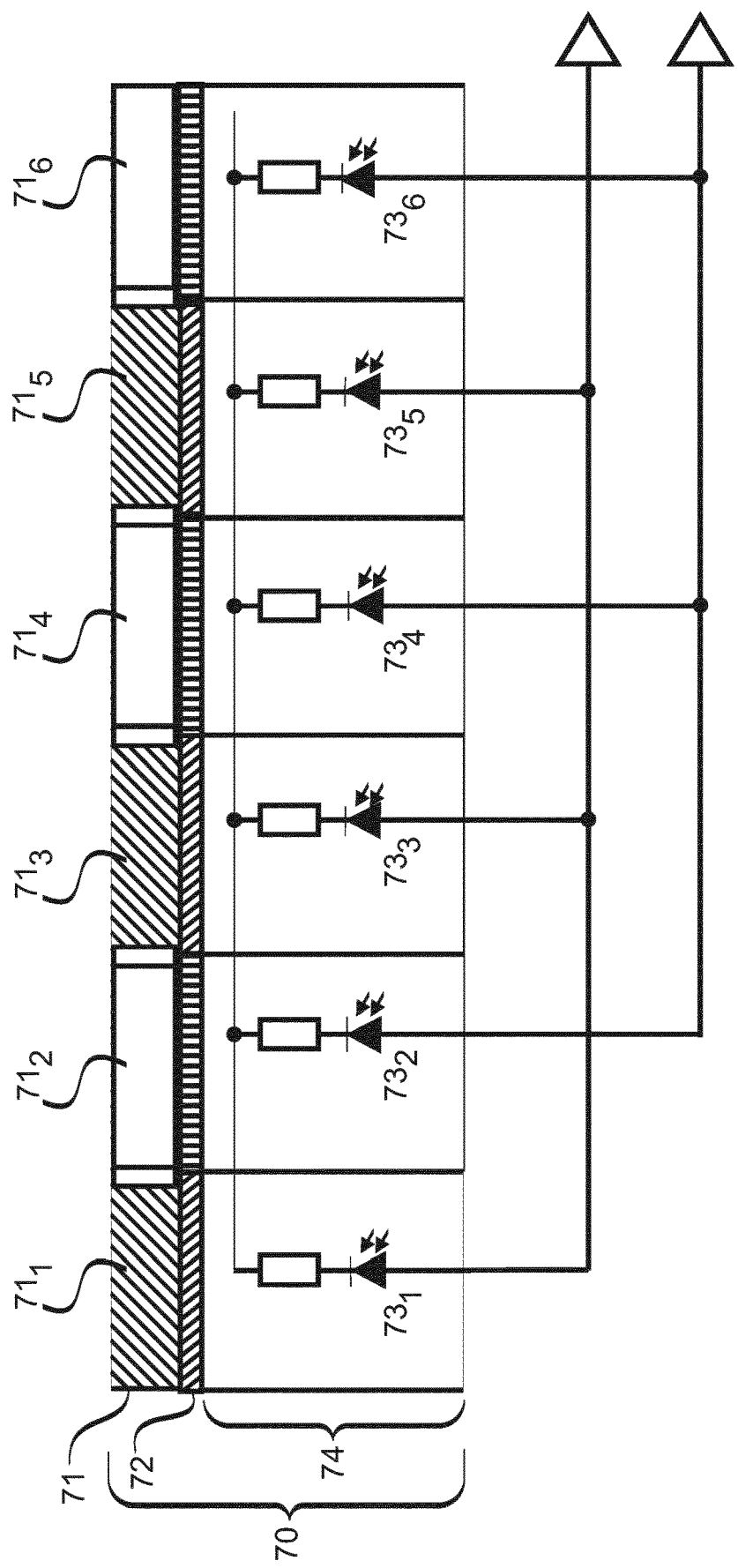
FIG. 10 illustrates schematically a further embodiment of an X-ray detector.

According to an embodiment (an example of which is illustrated in FIG. 10) of the first aspect, an X-ray detector 70 is provided. The X-ray detector further comprises a structured color filter layer 72 disposed in-between the structured scintillator layer 71 and the optical detector layer 74. The first scintillator element $71_1$ is configured to emit visible light having a first wavelength, and the second scintillator element $71_2$ is configured to emit visible light having a second wavelength. The structured color filter layer 72 is configured to filter the first and second visible light having respective wavelengths prior to detection in the optical detector layer 74, to improve crosstalk performance of the optical detector layer.

In FIG. 10, a cut-through schematic view of an X-ray detector according to this embodiment is shown. Scintillator slabs $71_1$, $71_3$, $71_5$ are provided as a first scintillator material emitting a first wavelength, and scintillator slabs $71_2$, $71_4$, and $71_6$ are provided as a second scintillator material emitting a second wavelength. The corresponding optical detection cells in the optical detector layer 74 are covered by an optical filter layer 72. The optical filter layer 72 comprises a plurality of color filters with first and second colors, each adequately tuned to the wavelength of the visible light emitted by the corresponding scintillator above. Optionally, the optical detection cells $73_1$, $73_2$, $73_3$, $73_4$, $73s$, $73_6$ are provided as silicon photomultipliers with active or passive quenching circuits (as illustrated in FIG. 9 with passive quenching resistors).

Figure 11:
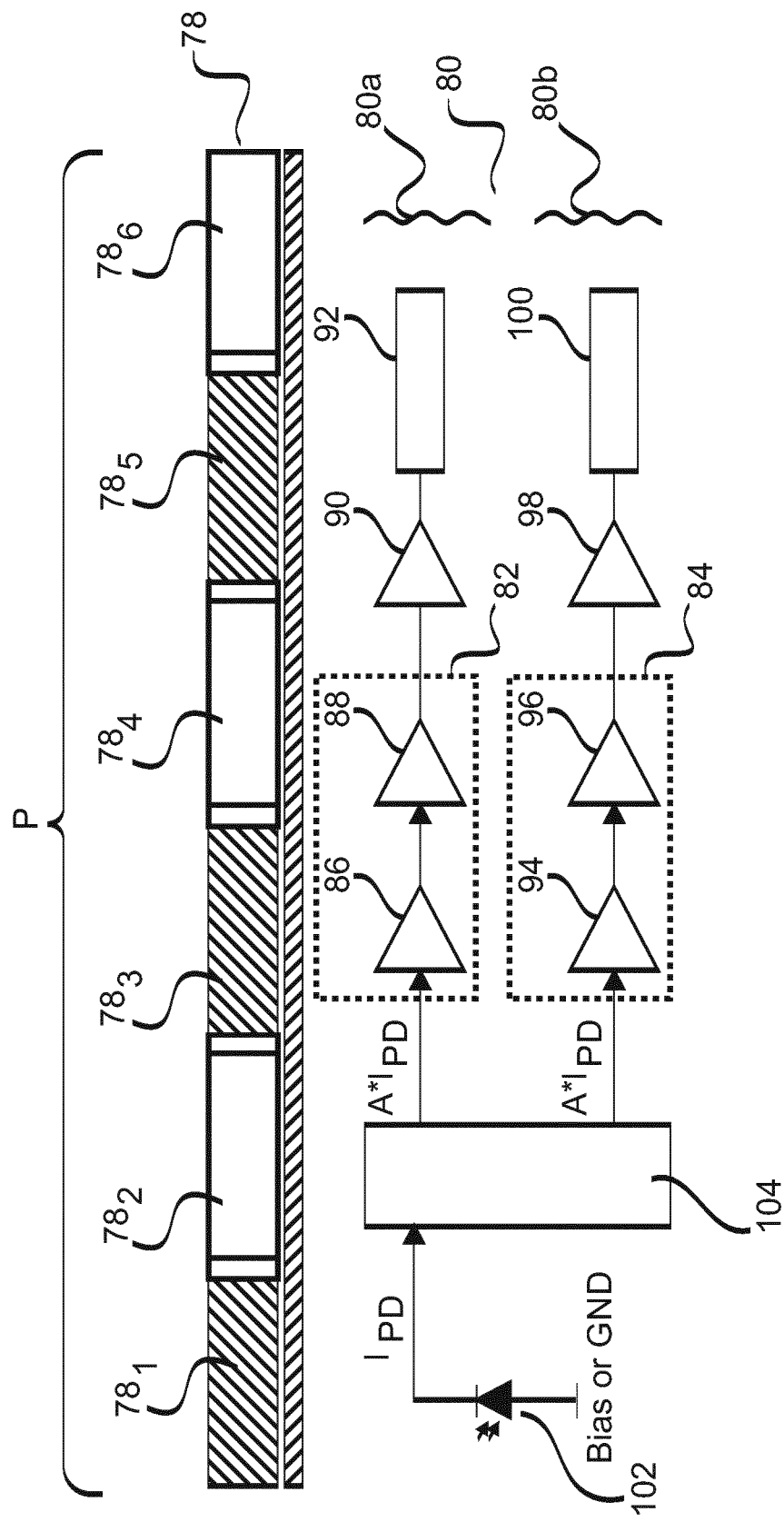
FIG. 11 illustrates schematically a single pixel having a plurality of detection channels.

FIG. 11 illustrates an alternative embodiment, comprising an X-ray detector 76 having a pixel P comprising a structured scintillator layer 78, wherein a first set of structured scintillators $78_1$, $78_3$, and $78_5$ is of a first type of scintillator material, and a second set of structured scintillators $78_2$, $78_4$, and $78_6$ is of a second type of scintillator material. The first and second types of scintillator material have different decay time constants. The optical detector layer further comprises an optical detection cell comprising a single photodiode per pixel P. Alternatively, the optical detection cell comprises a silicon photomultiplier with active or passive quenching circuits.

The optical detection layer 80 comprises a photodiode 102 connected to a two-channel photon counting front-end electronic circuit forming the signal combination arrangement. The photon counting front-end electronics has a first channel 80a sensitive to a first decay time constant, and a second channel 80b sensitive to a second decay time constant. Therefore, the front-end channels may separate events originating at either type of scintillator slab.

A fast channel 82 comprises a first amplifier 86 and a first shaper 88, in series with a discriminator 90 and a first counter 92. A slow channel 84 comprises a second amplifier 94, a second shaper 96, in series with a second amplifier 98 and a second counter 100.

In operation, the X-ray detector 76 illustrated in FIG. 11 comprises a fast shaper channel 82 configured to generate a pulse height of adequate amplitude for events which originate on a fast scintillator $78_1$, $78_3$, and $78_5$. A signal from the slow scintillator $78_2$, $78_4$, and $78_6$ will cause a large ballistic deficit, allowing the contribution from the slow scintillator to be disregarded. A discrimination of the pulse height of the faster scintillators enables account of the number of events originating on slabs of the same type. The difference of decay time constants of the scintillators is such that the resulting energy pedestal from the slow scintillator is sufficiently low to not significantly impair discrimination of fast events.

The slow shaper channel 82 produces acceptable signals from events produced by the slow scintillator. Optionally, the charge sensitive amplifier exhibits a slow slew rate thus filtering out events that could only be caused by the fast scintillators, which avoids excessive background charge from the fast scintillator.

Fast-slow architectures as described are able to separate optical photons which originated on structured scintillator slabs having different decay time constants. Optionally, a current mirror 104 is provided to replicate the photodiode current $I_{PD}$.

According to the present embodiment, the signal combination arrangement reads channels per pixel P. The number of readout channels optionally corresponds to the number of photon interactions of each scintillator type. For example, in the illustrated system with two types of scintillator material, two readout channels would be provided each counting the number of photon interactions from a respective different scintillator material. This topology is particularly applicable to photon counting electronics, in which only the number of events is registered, disregarding the energy of the X-ray photon. Optionally, the X-ray detector may be a multi-energy bin detector.

Optionally, the signal combination arrangement of FIG. 11 may be provided as a single charge sensitive amplifier (CSA) stage common to both shapers. The CSA is coupled to both shapers 88 and 96. The skilled person will appreciate that many different topologies may be used, having a similar functionality to that discussed above. Optionally, given a certain pixel size and the equivalent capacitance of the photodiode capacitor, the use of a CSA stage may not be necessary. If the equivalent input capacitance is small enough, the CSAs may be removed completely, providing a single-stage shaper topology. In this embodiment, a single photodiode per pixel is required. However, dependent on the chosen scintillator type and X-ray flux, further sub-pixelation may be provided.

Optionally, more than two structured scintillator slabs per fringe pitch are provided. For example, three structured scintillator slabs per fringe pitch may be provided. Alternatively, four structured scintillator slabs per fringe pitch may be provided. The number of optical detector cells, such as silicon photomultiplier cell groups or photodiodes should be increased proportionally, or alternatively scintillators with three or four different response times or scintillation wavelength should be employed. Employing more than two sample points per fringe pitch removes the need to phase step by moving the source grating $G_0$ or the phase grating $G_1$ in a larger X-ray phase-contrast imaging system.

Optionally, the signal combination arrangement provides the possibility to readout all slab signals or sub-pixel signals as individual signals, instead of summing them inside one pixel area. With individual readout of signals, the sub-pixel corresponding to each slab would be of the order of between 5 μm and 20 μm×250 μm in size. Phase and amplitude information can then be extracted by performing the addition of slab signals in the digital domain. This approach also allows the handling of fractional ratios of slab pitch and fringe pitch, for example, 2.4 slabs per fringe. In the digital domain, a multiplication with the cosine and sine of the expected fringe frequency and subsequent summing can provide the correct sum signal.

The signal combination arrangement 116 and its optional embodiments may be implemented in many different ways, which will now be discussed.

FIG. 5 illustrates a signal combination arrangement consisting of silicon photomultipliers of adjacent sub-pixels being connected in parallel to sum the output currents from adjacent sub-pixels. This signal combination arrangement consists of wiring and interconnection in between the silicon photomultipliers that can be provided, for example, by metal tracks deposited on a silicon substrate in a semiconductor manufacturing process.

With reference to FIG. 8, the signal combination arrangement 116 provides a network of bus lines and switches Hz and Vt. The complementary switching of switches Hz and Vt enables adjacent sub-pixels to be connected in parallel in the same way as in FIG. 5, however changing the settings of switches Hz and Vt causes the adjacent sub-pixel interconnection to be rotated by 90°. The switches Hz and Vt can be implemented, for example, as integrated silicon switches or integrated CMOS analogue switches.

FIG. 9 illustrates an embodiment in which the alternate sub-pixels are in optical communication with two types of scintillator slab $44_1$, $44_2$ having different decay time constants. First event validation filter 48a and second event validation filter 48b enable the separation of optical signals which have incorrectly entered and adjacent sub-pixel (as optical crosstalk). The first event validation filter 48a and the second event validation filter 40b can be implemented as an analogue filtering circuit using, for example, matched filters corresponding to the decay constant of the scintillator material being detected.

Alternatively, or in combination, the detection signals from the sub-pixels can be converted from analogue into digital format using an analogue to digital converter (ADC). First event validation filter 48a and second event validation filter 48b would then be provided as digital filters in a digital signal processing (DSP) module. The DSP module can be implemented in a field programmable gate array (FPGA), or an application-specific integrated circuit (ASIC). Alternatively or in combination, the DSP module can be implemented on a microprocessor or computer processor.

Therefore, the signal combination arrangement 116 discussed in the above embodiments can be provided in many different ways whilst retaining the disclosed functionality.

According to a second aspect, there is provided an interferometer 110 for phase-contrast or dark-field X-ray imaging. The interferometer comprises:
  a phase grating structure 112; and
  an X-ray detector 114a, 114b, 116 according to the first aspect or its embodiments described above.

The phase grating structure and X-ray detector are arranged in an optical path such that the phase grating structure and the structured scintillator layer of the X-ray detector form an interferometer arrangement for correlating X-ray radiation.

FIG. 3 illustrates the interferometer as the elements of FIG. 1 falling between bracket 110.

According to a third aspect, there is provided an X-ray imaging system 118 comprising:
  an X-ray source 120;
  an interferometer 110 according to the second aspect; and
  a controller 122.

The controller 122 is configured to activate the X-ray source 120 to illuminate an object of interest 126 positionable in an optical path with X-ray radiation 128. The X-ray detector 114a, 114b of the interferometer 110 is configured to sample and detect an X-ray wave front. The controller 122 is configured to electronically read out signals representing the fringe pattern from the plurality of sub-pixels of the X-ray detector 114a, 114b, 116 of the interferometer 110.

FIG. 3 illustrates the system 118 as the elements falling within the bracket 118.

Optionally, the controller 122 is an embedded computer, a personal computer PC, or another processing unit enabling the control of the X-ray system and the handling of the output information.

Optionally, the X-ray imaging system is an inverse X-ray phase-contrast imaging system in which the distance between a source grating G0 and a phase grating G1 is less than a distance between the phase grating G1 and the analyzer grating G2.

Optionally, the X-ray imaging system is an X-ray phase-contrast imaging system in which the distance between a source grating G0 and a phase grating G1 is greater than a distance between the phase grating G1 and the analyzer grating G2.

Optionally, the controller 122 is configured to prepare X-ray image output data from the signals electronically read out from the signal combination arrangement 116 of the X-ray detector 114a, 114b, 116 using a wide range of X-ray phase-contrast image reconstruction algorithms. The controller 122 may display X-ray image output data on an optionally included controller display (not shown), or alternatively can transmit the X-ray image output data to a server (not shown) or PACS system (not shown) for further use.

Optionally, the X-ray source 120 is a coherent x-ray source.

Optionally, an embodiment of the X-ray imaging system is provided having two modes. The signal combination arrangement 116 of the X-ray detector is configurable into a first mode in which the first and second output signals are required from the first set of adjacent sub-pixels, and configurable into a second mode in which the first and second output signals are required for a second set of adjacent sub-pixels, when first and second sets of sub-pixels are aligned at an angle with respect to each other, thus enabling sub-pixel accumulation in different orientations without adjusting the position of the X-ray detector.

Optionally, the angle that the first and second sets of sub-pixels are aligned at is 90° (in other words, the sub-pixels of the first and second sets of sub-pixels form a rectangular grid). Optionally, the first and second sets of sub-pixels are aligned at an interior angle of between 0° and 90° to each other. Optionally, the first and second sets of sub-pixels are aligned at an interior angle of between 0° and 60° to each other. Optionally, the first and second sets of sub-pixels are aligned at an interior angle of between 0° and 60° to each other. Optionally, the first and second sets of sub-pixels are aligned at an interior angle of between 0° and 30°.

In this embodiment of the system, the X-ray source 120 (and/or a source grating 124 ($G_0$)) incorporated in the X-ray source 120 are rotatable between a first axial state and a second axial state around an axis pointing from the X-ray source 120 towards the X-ray detector 114a, 114b, 116. When the signal combination arrangement 116 of the X-ray detector 114a, 114b, 116 is configured into its first mode, the X-ray source 120 is set in a first axial state. When the signal combination arrangement 116 of the X-ray detector 114a, 114b, 116 is configured into its second mode, the X-ray source 120 (and/or its source grating 124 ($G_0$)) is rotated into a second axial state which is rotated by substantially 90° (although a range of other angles could be used, as discussed above) clockwise, or anticlockwise around the axis compared to the first axial state. This enables the detection of fine structure at two preferred directions by rotating the X-ray source 120 and/or the source grating 124 ($G_0$). According to a fourth aspect, a method 130 is provided for phase contrast X-ray imaging and/or dark-field X-ray imaging, comprising the following steps:

a) generating 132 X-ray radiation to examine an object of interest, and directing the X-ray radiation towards an object of interest;

b) receiving at an X-ray detector 134 the X-ray radiation which has been phase-modulated by the object of interest;

c) converting 136 the modulated X-ray radiation into a plurality of optical slab signals using a structured scintillator layer comprising a plurality of slabs arranged to sample the incident fringe pattern;

d) detecting 138 the plurality of optical slab signals using an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer, wherein the optical detector layer further comprises a plurality of optical detection cells configured to provide a plurality of detection signals based on the presence of related optical slab signals;

e) electronically reading out 140 signals representing the fringe pattern from the plurality of sub-pixels using a signal combination arrangement,
  wherein the signal combination arrangement is configured to generate at least first and second output signals as combinations of the detection signals of the optical detection cells of the sub-pixels, wherein the at least first and second output signals are each proportional to a spatial signal amplitude due to the incident X-ray fringe pattern received on a respective slab of the structured scintillator layer, and wherein a pixel signal of the X-ray detector comprises at least first and second output signals acquired from at least two adjacent sub-pixels at a fringe sampling resolution defined by a width of the slabs.

Figure 12:
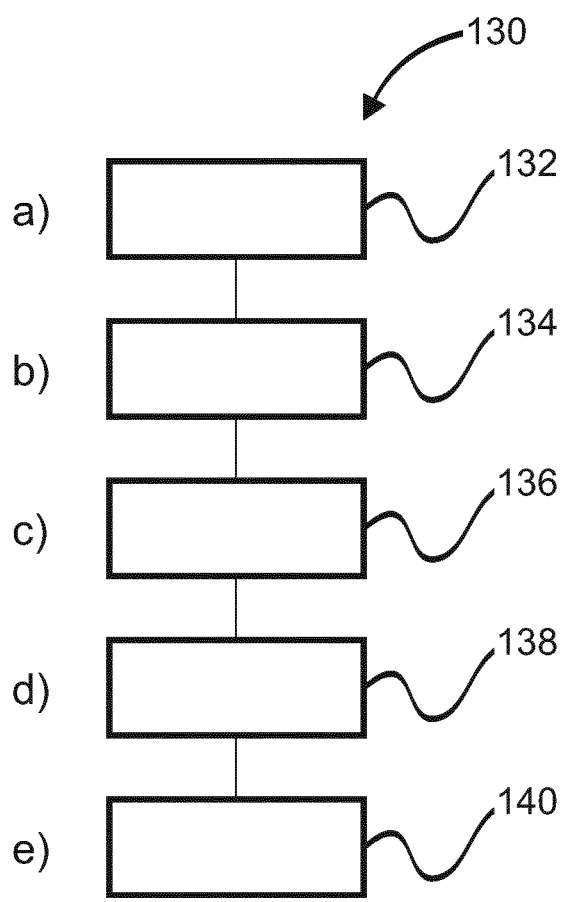
FIG. 12 illustrates a method according to the fourth aspect.

FIG. 12 illustrates the method according to the fourth aspect.

Optionally, an embodiment of the fourth aspect is provided having two modes. In step d1), the signal combination arrangement 116 of the X-ray detector is configured into a first mode in which the first and second output signals are required from the first set of adjacent sub-pixels.

In step e1), signals representing the fringe pattern in a first direction are electronically read out from the first set of adjacent sub-pixels using a signal combination arrangement.

In step d2), the signal combination arrangement of the X-ray detector is configured into a second mode in which the first and second output signals are required from the second set of adjacent sub-pixels, when first and second sets of sub-pixels are aligned at an angle with respect to each other.

In step e2), signals representing the fringe pattern in a second direction are electronically read out from the second set of adjacent sub-pixels using the signal combination arrangement.

It will be appreciated that a variety of readout sequences of the steps d1), d2), e1), and e2) may be contemplated. For example, the sequence d1), e1), d2), e2) may be preferred. Alternatively, the sequence d2), e2), d1), e1) may be applied.

Optionally, the angle that the first and second sets of sub-pixels are aligned at is 90° (in other words, the sub-pixels of the first and second sets of sub-pixels form a rectangular grid). Optionally, the first and second sets of sub-pixels are aligned at an interior angle of between 0° and 90° to each other. Optionally, the first and second sets of sub-pixels are aligned at an interior angle of between 0° and 80° to each other Optionally, the first and second sets of sub-pixels are aligned at an interior angle of between 0° and 60° to each other. Optionally, the first and second sets of sub-pixels are aligned at an interior angle of between 0° and 30°.

According to a fifth aspect, there is provided a computer program element for controlling the X-ray imaging system of the third aspect, which, when being executed by processing unit, is adapted to perform the method steps of the fourth aspect.

According to a sixth aspect, there is provided a computer readable medium having stored in the computer program element of the fifth aspect.

A computer program element might therefore be stored on a computer unit, which might also be an embodiment of the present invention. This computing unit may be adapted to perform or induce performance of the steps of the method described above. Moreover, it may be adapted to operate the components of the above-described apparatus. The computing unit can be adapted to operate automatically and/or to execute orders of a user. A computer program may be loaded into a working memory of a data processor. The data processor may thus be equipped to carry out the method of the invention.

This exemplary embodiment of the invention covers both the computer program that has the intervention installed from the beginning, and a computer program that by means of an update turns an existing program into a program that uses the invention.

A computer program may be stored and/or distributed on a suitable medium, such as optical storage media, or a solid state medium supplied together with, or as a part of other hardware, but may also be distributed in other forms, such as via the Internet or other wired or wireless telecommunication systems. However, the computer program may also be presented over a network like the World Wide Web, and can also be downloaded into the working memory of a data processor from such a network.

According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, also other combinations between features relating to different subject-matters is considered to be disclosed with this application. All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments. Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An X-ray detector for sampling an incident X-ray fringe pattern in phase contrast and/or dark-field X-ray imaging, comprising:
   a structured scintillator layer comprising a plurality of slabs arranged to sample the incident fringe pattern and convert it into a plurality of optical slab signals;
   an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer; and
   a signal combination arrangement arranged to electronically read-out signals representing the fringe pattern from the plurality of sub-pixels;
   wherein the sub-pixels further comprise a plurality of optical detection cells configured to provide a plurality of detection signals based on the presence of related optical slab signals;
   wherein the signal combination arrangement is configured to enable the acquisition of phase contrast and/or dark field X-ray images at a first and second detection direction without adjusting the position of the X-ray detector, by generating at least first and second output signals as combinations of the detection signals of the optical detection cells of the optical detector layer, wherein the at least first and second output signals are each proportional to a spatial signal amplitude due to the incident X-ray fringe pattern received on a respective slab of the structured scintillator layer, and wherein a pixel signal of the X-ray detector comprises at least first and second output signals acquired from at least two adjacent sub-pixels at a fringe sampling resolution defined by a width of the slabs.

2. The X-ray detector according to claim 1, wherein the optical detection cell comprises one, or a plurality, of a silicon photomultipliers configured to detect the respective optical slab signal emitted from the respective slab of the structured scintillator layer.

3. The X-ray detector according to claim 1, wherein the signal combination arrangement is configurable into a first mode in which the first and second output signals are acquired from a first set of adjacent sub-pixels, and configurable into a second mode in which the first and second output signals are acquired from a second set of adjacent sub-pixels, wherein the first and second sets of sub-pixels are aligned at an angle with respect to each other, thus enabling sub-pixel accumulation in different directions without adjusting the position of the X-ray detector.

4. The X-ray detector according to claim 1, wherein the plurality of optical detection cells in one sub-pixel is electrically connected in parallel to generate, in operation, a signal proportional to the number of optical detection cells triggered by an optical emission from a slab of the structured scintillator layer.

5. The X-ray detector according to claim 1,
wherein the structured scintillator layer further comprises a first scintillator element and a second scintillator element, each formed from different scintillator materials having a different decay time constant to each other, and
wherein the signal combination arrangement further comprises a first and a second event validation filter matched to the different decay time constants of the first and second scintillator elements; to discriminate whether or not the first and second optical detector signals result from optical crosstalk.

6. The X-ray detector according to claim 5, wherein the signal combination arrangement further comprises a complementary event validation filter associated with each sub-pixel, configured to provide a signal related to an optical emission from a neighboring sub-pixel to the neighboring sub-pixel.

7. The X-ray detector according to claim 1, further comprising:
a structured color filter layer disposed in-between the structured scintillator layer and the optical detector layer;
wherein the first scintillator element is configured to emit visible light having a first wavelength, and the second scintillator element is configured to emit visible light having a second wavelength, and the structured color filter layer is configured to filter the first and second visible light having respective wavelengths prior to detection in the optical detector layer to improve crosstalk performance of the optical detector layer.

8. The X-ray detector according to claim 1, further comprising:
a scintillator isolation arrangement formed in the structured scintillator layer as an optically-isolating matrix surrounding each slab to improve crosstalk performance of the optical detector layer.

9. The X-ray detector according to claim 1, wherein the slab width is in the range 0.5 to 50 micrometers.

10. The X-ray detector according to claim 1, wherein the structured scintillator layer comprises third or fourth scintillator elements, and the optical detector layer comprises third or fourth sub-pixels, each in optical alignment with the third or fourth scintillator elements to improve a fringe sampling resolution.

11. An interferometer for phase contrast or dark-field X-ray imaging, comprising:
a phase grating structure, and
an X-ray detector comprising:
a structured scintillator layer comprising a plurality of slabs arranged to sample the incident fringe pattern and convert it into a plurality of optical slab signals;
an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer; and
a signal combination arrangement arranged to electronically read-out signals representing the fringe pattern from the plurality of sub-pixels;
wherein the sub-pixels further comprise a plurality of optical detection cells configured to provide a plurality of detection signals based on the presence of related optical slab signals;
wherein the signal combination arrangement is configured to enable the acquisition of phase contrast and/or dark field X-ray images at a first and second detection direction without adjusting the position of the X-ray detector by generating at least first and second output signals as combinations of the detection signals of the optical detection cells of the optical detector layer, wherein the at least first and second output signals are each proportional to a spatial signal amplitude due to the incident X-ray fringe pattern received on a respective slab of the structured scintillator layer, and wherein a pixel signal of the X-ray detector comprises at least first and second output signals acquired from at least two adjacent sub-pixels at a fringe sampling resolution defined by a width of the slabs;
wherein the phase grating structure and the X-ray detector are arranged in an optical path such that the phase grating structure and the scintillator layer of the X-ray detector form an interferometer arrangement for correlating X-ray radiation.

12. An X-ray imaging system, comprising:
an X-ray source;
an interferometer comprising:
a phase grating structure, and
an X-ray detector comprising:
a structured scintillator layer comprising a plurality of slabs arranged to sample the incident fringe pattern and convert it into a plurality of optical slab signals;
an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer; and a signal combination arrangement arranged to electronically read-out signals representing the fringe pattern from the plurality of sub-pixels;

wherein the sub-pixels further comprise a plurality of optical detection cells configured to provide a plurality of detection signals based on the presence of related optical slab signals;

wherein the signal combination arrangement is configured to enable the acquisition of phase contrast and/or dark field X-ray images at a first and second detection direction without adjusting the position of the X-ray detector by generating at least first and second output signals as combinations of the detection signals of the optical detection cells of the optical detector layer, wherein the at least first and second output signals are each proportional to a spatial signal amplitude due to the incident X-ray fringe pattern received on a respective slab of the structured scintillator layer, and wherein a pixel signal of the X-ray detector comprises at least first and second output signals acquired from at least two adjacent sub-pixels at a fringe sampling resolution defined by a width of the slabs;

wherein the phase grating structure and the X-ray detector are arranged in an optical path such that the phase grating structure and the scintillator layer of the X-ray detector form an interferometer arrangement for correlating X-ray radiation; and a controller;

wherein the controller is configured to activate the X-ray source to apply X-ray radiation to an object of interest positionable in the optical path;

wherein the X-ray detector of the interferometer is configured to sample and detect an X-ray wave front; and wherein the controller is configured to electronically read-out signals representing the fringe pattern from the plurality of sub-pixels of the X-ray detector of the interferometer.

13. A method for phase contrast X-ray imaging and/or dark-field X-ray imaging, comprising:

generating X ray radiation to examine an object of interest, and directing the X-ray radiation towards an object of interest;

receiving at an X-ray detector the X-ray radiation which has been phase-modulated by the object of interest;

converting the modulated X-ray radiation into a plurality of optical slab signals using a structured scintillator layer comprising a plurality of slabs arranged to sample the incident fringe pattern;

detecting the plurality of optical slab signals using an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer, wherein the optical detector layer further comprises a plurality of optical detection cells configured to provide a plurality of detection signals based on the presence of related optical slab signals; and electronically reading out signals representing the fringe pattern from the plurality of sub-pixels using a signal combination arrangement, wherein the signal combination arrangement is configured to enable the acquisition of phase contrast and/or dark field X-ray images at a first and second detection direction without adjusting the position of the X-ray detector by generating at least first and second output signals as combinations of the detection signals of the optical detection cells of the optical detector layer, wherein the at least first and second output signals are each proportional to a spatial signal amplitude due to the incident X-ray fringe pattern received on a respective slab of the structured scintillator layer, and wherein a pixel signal of the X-ray detector comprises at least first and second output signals acquired from at least two adjacent sub-pixels at a fringe sampling resolution defined by a width of the slabs.

14. A non-transitory computer-readable medium having one or more executable instructions, which, when executed by a processor, cause the processor to perform a method for phase contrast X-ray imaging and/or dark-field X-ray imaging, the method comprising:

generating X-ray radiation to examine an object of interest, and directing the X-ray radiation towards an object of interest;

receiving at an X-ray detector the X-ray radiation which has been phase-modulated by the object of interest;

converting the modulated X-ray radiation into a plurality of optical slab signals using a structured scintillator layer comprising a plurality of slabs arranged to sample the incident fringe pattern;

detecting the plurality of optical slab signals using an optical detector layer in optical communication with the structured scintillator layer comprising a plurality of sub-pixels, wherein each sub-pixel is aligned with a respective slab of the structured scintillator layer to detect a respective optical slab signal emitted from the respective slab of the structured scintillator layer, wherein the optical detector layer further comprises a plurality of optical detection cells configured to provide a plurality of detection signals based on the presence of related optical slab signals; and electronically reading out signals representing the fringe pattern from the plurality of sub-pixels using a signal combination arrangement, wherein the signal combination arrangement is configured to enable the acquisition of phase contrast and/or dark field X-ray images at a first and second detection direction without adjusting the position of the X-ray detector by generating at least first and second output signals as combinations of the detection signals of the optical detection cells of the optical detector layer, wherein the at least first and second output signals are each proportional to a spatial signal amplitude due to the incident X-ray fringe pattern received on a respective slab of the structured scintillator layer, and wherein a pixel signal of the X-ray detector comprises at least first and second output signals acquired from at least two adjacent sub-pixels at a fringe sampling resolution defined by a width of the slabs.

* * * * *